(12) United States Patent
Lukyanov et al.

(10) Patent No.: US 8,563,703 B2
(45) Date of Patent: *Oct. 22, 2013

(54) FLUORESCENT PROTEINS AND METHODS FOR USING SAME

(75) Inventors: Sergey A. Lukyanov, Moscow (RU); Dmitry M. Chudakov, Moscow (RU)

(73) Assignee: Evrogen IP Joint Stock Company, Moscow (RU)

( * ) Notice: Subject to any disclaimer, the term of this patent is extended or adjusted under 35 U.S.C. 154(b) by 35 days.

This patent is subject to a terminal disclaimer.

(21) Appl. No.: 13/365,137

(22) Filed: Feb. 2, 2012

(65) Prior Publication Data

US 2013/0203162 A1    Aug. 8, 2013

Related U.S. Application Data

(62) Division of application No. 12/619,488, filed on Nov. 16, 2009, now Pat. No. 8,138,320, which is a division of application No. 11/651,728, filed on Jan. 9, 2007, now Pat. No. 7,638,615.

(60) Provisional application No. 60/761,807, filed on Jan. 25, 2006.

(51) Int. Cl.
*C07H 21/02* (2006.01)

(52) U.S. Cl.
USPC ... 536/23.1; 536/23.5; 435/320.1; 435/252.3; 435/325

(58) Field of Classification Search
None
See application file for complete search history.

(56) References Cited

U.S. PATENT DOCUMENTS

| | | |
|---|---|---|
| 5,182,202 A | 1/1993 | Kajiyama et al. |
| 5,221,623 A | 6/1993 | Legocki et al. |
| 5,229,285 A | 7/1993 | Kajiyama et al. |
| 5,330,906 A | 7/1994 | Kajiyama et al. |
| 5,418,155 A | 5/1995 | Cormier et al. |
| 5,439,797 A | 8/1995 | Tsien et al. |
| 5,484,956 A | 1/1996 | Lundquist et al. |
| 5,538,879 A | 7/1996 | Muller-Rober et al. |
| 5,576,198 A | 11/1996 | McBride et al. |
| 5,595,896 A | 1/1997 | Coruzzi et al. |
| 5,618,722 A | 4/1997 | Zenno et al. |
| 5,629,470 A | 5/1997 | Lam et al. |
| 5,633,155 A | 5/1997 | Kim et al. |
| 5,650,135 A | 7/1997 | Contag et al. |
| 5,656,466 A | 8/1997 | Moon et al. |
| 5,674,713 A | 10/1997 | McElroy et al. |
| 5,674,731 A | 10/1997 | Lin et al. |

(Continued)

FOREIGN PATENT DOCUMENTS

| WO | WO-0002997 | 1/2000 |
|---|---|---|
| WO | WO-0003245 A1 | 1/2000 |

(Continued)

*Primary Examiner* — Cecilia J. Tsang
*Assistant Examiner* — Randall L Beane
(74) *Attorney, Agent, or Firm* — Patterson & Sheridan, LLP

(57) ABSTRACT

The present invention provides nucleic acid molecules encoding novel red fluorescent proteins from *Entacmaea quadricolor* and mutants thereof. Also of interest are proteins that are substantially similar to the novel red fluorescent proteins. In addition, host cells, stable cell lines and transgenic organisms comprising the nucleic acid molecules encoding the novel red fluorescent proteins are provided. The subject proteins and nucleic acid compositions find use in a variety of different applications and methods, particularly for labeling of biomolecules, cells, or cell organelles. Finally, kits for use in such methods and applications are provided.

9 Claims, 7 Drawing Sheets

(56) References Cited

U.S. PATENT DOCUMENTS

| | | |
|---|---|---|
| 5,688,648 A | 11/1997 | Mathies et al. |
| 5,689,045 A | 11/1997 | Logemann et al. |
| 5,689,049 A | 11/1997 | Cigan et al. |
| 5,700,673 A | 12/1997 | McElroy et al. |
| 5,707,804 A | 1/1998 | Mathies et al. |
| 5,728,528 A | 3/1998 | Mathies et al. |
| 5,739,409 A | 4/1998 | Fischer et al. |
| 5,750,870 A | 5/1998 | Mathews et al. |
| 5,767,367 A | 6/1998 | Dudits et al. |
| 5,795,737 A | 8/1998 | Seed et al. |
| 5,804,387 A | 9/1998 | Cormack et al. |
| 5,824,485 A | 10/1998 | Thompson et al. |
| 5,843,746 A | 12/1998 | Tatsumi et al. |
| 5,863,727 A | 1/1999 | Lee et al. |
| 5,866,336 A | 2/1999 | Nazarenko et al. |
| 5,869,255 A | 2/1999 | Mathies et al. |
| 5,911,952 A | 6/1999 | Tsuji |
| 5,945,283 A | 8/1999 | Kwok et al. |
| 5,945,526 A | 8/1999 | Lee et al. |
| 5,968,738 A | 10/1999 | Anderson et al. |
| 5,972,638 A | 10/1999 | Burlage et al. |
| 5,981,200 A | 11/1999 | Tsien et al. |
| 5,989,835 A | 11/1999 | Dunlay et al. |
| 5,998,146 A | 12/1999 | Latva et al. |
| 6,008,373 A | 12/1999 | Waggoner et al. |
| 6,130,313 A | 10/2000 | Li et al. |
| 6,469,154 B1 | 10/2002 | Tsien et al. |
| 6,699,687 B1 | 3/2004 | Tsien et al. |
| 7,638,615 B1 | 12/2009 | Lukyanov et al. |
| 8,138,320 B2 | 3/2012 | Lukyanov et al. |

FOREIGN PATENT DOCUMENTS

| | | |
|---|---|---|
| WO | WO-0017624 A2 | 3/2000 |
| WO | WO-0017643 A2 | 3/2000 |
| WO | WO-0026408 A2 | 5/2000 |
| WO | WO-02068459 A2 | 9/2002 |
| WO | WO 2007085923 A2 * | 8/2007 |

* cited by examiner

```
SEQ ID NO:2  (EqFP578)    : ...MSELIKENMHMKLYMEGTVNNHHFKCTSEGERKPYEGTQT:40
SEQ ID NO:4  (EqFP578m1)  : ...MSELIKENMHMKLYMEGTVNNHHFKCTSEGEKPYEGTQT:40
SEQ ID NO:6  (M1-NA)      : MGEYSELITENMHMKLYMEGTVNNHHFKCTSEGEKPYEGTQT:43
SEQ ID NO:8  (M1-602)     : MGEDSELITENMHMKLYMEGTVNNHHFKCTSEGEKPYEGTQT:43
SEQ ID NO:10 (M1-637)     : MGEDSELITENMHMKLYMEGTVNNHHFKCTSEGEKPYEGTQT:43
SEQ ID NO:12 (M1-mono1)   : ...MSELIKENMHMKLYMEGTVNNHHFKCTSEGEKPYEGTQT:40
SEQ ID NO:14 (nrM181-5)   : ...MSELIKENMHMKLYMEGTVNNHHFKCTSEGEKPYEGTQT:40
SEQ ID NO:16 (Cyan2-1)    : ...MSELIKENMHMKLYMEGTVNNHHFKCTSEGEKPYGGTQT:40

SEQ ID NO:2  (EqFP578)    : MKIKVVEGGPLPFAFDILATSFMYGSKTFINHTQGIPDLFKQS:83
SEQ ID NO:4  (EqFP578m1)  : MKIKVVEGGPLPFAFDILATSFMYGSKAFINHTQGIPDLFKQS:83
SEQ ID NO:6  (M1-NA)      : MKIKVVEGGPLPFAFDILATSFMYGSKAFINHTQGIPDLFKQS:86
SEQ ID NO:8  (M1-602)     : MKIKVVEGGPLPFAFDILATSFMYGSKAFINHTQGIPDLFKQS:86
SEQ ID NO:10 (M1-637)     : MKIKVVEGGPLPFAFDILATSFMYGSKAFINHTQGIPDLFKQS:86
SEQ ID NO:12 (M1-mono1)   : MRIKVVEGGPLPFAFDILATSFMYGSRTFINHTQGIPDLFKQS:83
SEQ ID NO:14 (nrM181-5)   : MKIKVVEGGPLPFAFDILATSFMYGSKTFINHTQGIPDLFKQS:83
SEQ ID NO:16 (Cyan2-1)    : MRIKVVEGGPLPVAFDILATSFMYGSRTFINHTQGIPDLFKQS:83

SEQ ID NO:2  (EqFP578)    : FPEGFTWERITTYEDGGVLTATQDTSLQNGCIIYNVKIRGVNF:126
SEQ ID NO:4  (EqFP578m1)  : FPEGFTWERITTYEDGGVLTATQDTSFQNGCIIYNVKIRGVNF:126
SEQ ID NO:6  (M1-NA)      : FPEGFTWERITTYEDGGVLTATQDTSFQNGCIIYNVKIRGVNF:129
SEQ ID NO:8  (M1-602)     : FPEGFTWERITTYEDGGVLTATQDTSLQNGCLIYNVKIRGVNF:129
SEQ ID NO:10 (M1-637)     : FPEGFTWERITTYEDGGVLTATQDTSLQNGCLIYNVKIRGVNF:129
SEQ ID NO:12 (M1-mono1)   : FPEGFTWERVTTYEDGGVLTATQDTSQDGCLIYNVKIRGVNF:126
SEQ ID NO:14 (nrM181-5)   : FPEGFTWERVTTYEDGGVLTATQDTSQDGCLIYNVKIRGVNF:126
SEQ ID NO:16 (Cyan2-1)    : FPEGFTWERVTTYEDGGVLTATQDTSQDGCLIYNVKIRGVNF:126

SEQ ID NO:2  (EqFP578)    : PSNGSVMQKKTLGWEANTEMLYPADGGLKGEIMALKLVGGGY:169
SEQ ID NO:4  (EqFP578m1)  : PSNGSVMQKKTRGWEANTEMLYPADGGLKGEIMALKLVGGGY:169
SEQ ID NO:6  (M1-NA)      : PSNGSVMQKKTRGWEANTEMLYPADGGLKGEIMALKLVGGGY:172
SEQ ID NO:8  (M1-602)     : PSNGSVMQKKTLGWEASTEMLYPADSGLKGEIMALKLVGGGY:172
SEQ ID NO:10 (M1-637)     : PSNGSVMQKKTLGWEASTEMLYPADSGLKGEIMALKLVGGGY:172
SEQ ID NO:12 (M1-mono1)   : PSNGSVMQKKTLGWEANTEMLYPADGGLECRDMALKLVGGGH:169
SEQ ID NO:14 (nrM181-5)   : PSNGSVMQKKTLGWEAHTEMLYPADGGLECRDMALKLVGGGH:169
SEQ ID NO:16 (Cyan2-1)    : PSNGSVMQKKTLGWEAFTEMLYPADGGLECRDMALKLVGGGH:169

SEQ ID NO:2  (EqFP578)    : LHSKTTYRSKKPAKNLKMPGFHFVDRRLERIKEADKETYVE:212
SEQ ID NO:4  (EqFP578m1)  : LHSKTTYRSKKPAKNLKMPGFHFVDRRLERIKEADKETYVE:212
SEQ ID NO:6  (M1-NA)      : LHSLKTTYRSKKPAKNLRMPGFHFVDRRLERIKEADKETYVE:215
SEQ ID NO:8  (M1-602)     : LHSLKTTYRSKKPAKNLKMPGFHFVDRRLERIKEADKETYVE:215
SEQ ID NO:10 (M1-637)     : LHSLKTTYRSKKPAKNLKMPGFHFVDRRLERIKEADKETYVE:215
SEQ ID NO:12 (M1-mono1)   : LISNKTTYRSKKPAKNLKMPGVYYVDRRLERIKEADKETYVE:212
SEQ ID NO:14 (nrM181-5)   : LIANKTTYRSKKPAKNLKMPGVYYVDRRLERIKEADKETYVE:212
SEQ ID NO:16 (Cyan2-1)    : LISNKTTYRSKKPAKNLKMPGVYYVDYRLERIKEADKETYVE:212

SEQ ID NO:2  (EqFP578)    : QHEMAVAKYCDLPSKLGH...:231
SEQ ID NO:4  (EqFP578m1)  : QHEMAVAKYCDLPSKLGH...:231
SEQ ID NO:6  (M1-NA)      : QHEMAVAKYCDLPSKLGHS..:234
SEQ ID NO:8  (M1-602)     : QHEMAVAKYCDLPSKLGHS..:234
SEQ ID NO:10 (M1-637)     : QHEMAVAKYCDLPSKLGHS..:234
SEQ ID NO:12 (M1-mono1)   : QHEVAVARYCDLPSKLGH...:231
SEQ ID NO:14 (nrM181-5)   : QHEMAVAKYCDLPSKLGHKLN:233
SEQ ID NO:16 (Cyan2-1)    : QHEVAVARYCDLPSKLGHKLN:233
```

Fig. 1

SEQUENCE LISTING

```
<160> NUMBER OF SEQ ID NOS: 18

<210> SEQ ID NO 1
<211> LENGTH: 696
<212> TYPE: DNA
<213> ORGANISM: Entacmaea quadricolor

<400> SEQUENCE: 1
atgagtgaac tgatcaaaga aaacatgcac atgaagctgt acatggaagg tacggtcaat      60
aaccaccatt tcaaatgcac gtctgaaggt gaacgcaagc catacgaagg aactcaaacc     120
atgaagatca aagtcgtcga gggaggacct ctgccatttg cctttgacat tcttgcgaca     180
agcttcatgt acggcagcaa gacttttatc aatcacactc aaggcattcc tgacttgttt     240
aagcagtcat tcctgaagg ttttacttgg gaaagaatta acatacga ggatggggga        300 gtccttactg ctacgcaaga caccagcctt caaaatggct gtatcattta acgtcaag       360 atcaatggag taaactttcc ttcaaatggt tctgtgatgc aaaagaagac tcttggttgg     420
gaggccaata cagagatgct gtatccagca gatggtggtc tgagggggaca ctcccaaatg    480 gcactaaagc ttgttggtgg tggctatctg cattgctctt tcaaaacaac ttacaggtca     540
aaaaagcctg cgaagaattt gaagatgccc ggtttccatt tgttgatca ccgtttagaa      600 aggataaagg aggctgacaa agaaacgtac gtggaacaac acgaaatggc agttgccaag     660
tactgtgacc ttccatccaa actgggacat cgttaa                               696

<210> SEQ ID NO 2
<211> LENGTH: 231
<212> TYPE: PRT
<213> ORGANISM: Entacmaea quadricolor

<400> SEQUENCE: 2

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Arg
                20                  25                  30

Lys Pro Tyr Glu Gly Thr Gln Thr Met Lys Ile Lys Val Val Glu Gly
            35                  40                  45

Gly Pro Leu Pro Phe Ala Phe Asp Ile Leu Ala Thr Ser Phe Met Tyr
        50                  55                  60

Gly Ser Lys Thr Phe Ile Asn His Thr Gln Gly Ile Pro Asp Leu Phe
65                  70                  75                  80

Lys Gln Ser Phe Pro Glu Gly Phe Thr Trp Glu Arg Ile Thr Thr Tyr
                85                  90                  95

Glu Asp Gly Gly Val Leu Thr Ala Thr Gln Asp Thr Ser Leu Gln Asn
            100                 105                 110

Gly Cys Ile Ile Tyr Asn Val Lys Ile Asn Gly Val Asn Phe Pro Ser
        115                 120                 125

Asn Gly Ser Val Met Gln Lys Lys Thr Leu Gly Trp Glu Ala Asn Thr
130                 135                 140
```

Glu Met Leu Tyr Pro Ala Asp Gly Gly Leu Arg Gly His Ser Gln Met
145                 150                 155                 160

Ala Leu Lys Leu Val Gly Gly Tyr Leu His Cys Ser Phe Lys Thr
            165                 170                 175

Thr Tyr Arg Ser Lys Lys Pro Ala Lys Asn Leu Lys Met Pro Gly Phe
            180                 185                 190

His Phe Val Asp His Arg Leu Glu Arg Ile Lys Glu Ala Asp Lys Glu
                195                 200                 205

Thr Tyr Val Glu Gln His Glu Met Ala Val Ala Lys Tyr Cys Asp Leu
            210                 215                 220

Pro Ser Lys Leu Gly His Arg
225                 230

<210> SEQ ID NO 3
<211> LENGTH: 696
<212> TYPE: DNA
<213> ORGANISM: Artificial sequence
<220> FEATURE:
<223> OTHER INFORMATION: eqFP578m1 nucleotide sequence

<400> SEQUENCE: 3
atgagcgagc tgatcaagga gaacatgcac atgaagctgt acatggaggg caccgtgaac      60
aaccaccact tcaagtgcac atccgagggc gaaggcaagc cctacgaggg cacccagacc     120
atgaagatca aggtggtcga gggcggccct ctccccttcg ccttcgacat cctggctacc     180
agcttcatgt acggcagcaa agccttcatc aaccacaccc agggcatccc cgacttcttt     240
aagcagtcct tccctgaggg cttcacatgg gagagaatca ccacatacga agacggggc     300
gtgctgaccg ctacccagga caccagcttc cagaacggct gcatcatcta caacgtcaag     360
atcaacgggg tgaacttccc atccaacggc cctgtgatgc agaagaaaac acgcggctgg     420
gaggccaaca ccgagatgct gtaccccgct gacggcggcc tgagaggcca cagccagatg     480
gccctgaagc tcgtgggcgg gggctacctg cactgctcct tcaagaccac atacagatcc     540
aagaaacccg ctaagaacct caagatgccc ggcttccact cgtggacca gactggaa       600
agaatcaagg aggccgacaa agagacctac gtcgagcagc acgagatggc tgtggccaag     660
tactgcgacc tccctagcaa actggggcac agatga                                696

<210> SEQ ID NO 4
<211> LENGTH: 231
<212> TYPE: PRT
<213> ORGANISM: Artificial sequence
<220> FEATURE:
<223> OTHER INFORMATION: eqFP578m1 amino acid sequence

<400> SEQUENCE: 4

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Lys Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Lys Ala Phe Ile Asn His Thr Gln Gly Ile Pro Asp Phe Phe
65                  70                  75                  80

Lys Gln Ser Phe Pro Glu Gly Phe Thr Trp Glu Arg Ile Thr Thr Tyr
                85                  90                  95

Glu Asp Gly Gly Val Leu Thr Ala Thr Gln Asp Thr Ser Phe Gln Asn
            100                 105                 110

Gly Cys Ile Ile Tyr Asn Val Lys Ile Asn Gly Val Asn Phe Pro Ser
        115                 120                 125

Asn Gly Pro Val Met Gln Lys Lys Thr Arg Gly Trp Glu Ala Asn Thr
    130                 135                 140

Glu Met Leu Tyr Pro Ala Asp Gly Leu Arg Gly His Ser Gln Met
145                 150                 155                 160

Ala Leu Lys Leu Val Gly Gly Tyr Leu His Cys Ser Phe Lys Thr
                165                 170                 175

Thr Tyr Arg Ser Lys Lys Pro Ala Lys Asn Leu Lys Met Pro Gly Phe
            180                 185                 190

His Phe Val Asp His Arg Leu Glu Arg Ile Lys Glu Ala Asp Lys Glu
        195                 200                 205

Thr Tyr Val Glu Gln His Glu Met Ala Val Ala Lys Tyr Cys Asp Leu
    210                 215                 220

Pro Ser Lys Leu Gly His Arg
225                 230

<210> SEQ ID NO 5
<211> LENGTH: 705
<212> TYPE: DNA
<213> ORGANISM: Artificial sequence
<220> FEATURE:
<223> OTHER INFORMATION: M1-NA mutant fluorescent protein nucleotide
      sequence

<400> SEQUENCE: 5
atgggtgagt atagcgagct gatcaccgag aacatgcaca tgaagctgta catggagggc        60
accgtgaaca accaccactt caagtgcaca tccgagggcg aaggcaagcc ctacgagggc       120
acccagacca tgaagatcaa ggtggtcgag ggcggccctc tccccttcgc cttcgacatc       180
ctggctacca gcttcatgta cggcagcaaa gccttcatca accacaccca gggcatcccc       240
gacttcttta gcagtccctt ccctgagggc ttcacatggg agagaatcac cacatacgaa       300 gacggggggcg tgctgactgc taccccaggac accagcttcc agaacggctg catcatctac       360
aacgtcaaga tcaacggggt gaacttccca tccaacggcc ctgtgatgca agaagaaaca       420
cgcggctggg aggccaacac cgagatgctg taccccgctg acggcggcct gagaggccac       480
agccagatgg ccctgaagct cgtgggcggg ggctacctgc actgctcctt caagaccaca       540
tacagatcca gaaacccgc taagaacctc aggatgcccg gcttccactt cgtggaccac       600
agactggaaa gaatcaagga agccgacaaa gagacctacg tcgagcagca cgagatggct       660
gtggccaagt actgcgacct ccctagcaaa ctggggcaca gctga                      705

<210> SEQ ID NO 6
<211> LENGTH: 234
<212> TYPE: PRT
<213> ORGANISM: Artificial sequence
<220> FEATURE:
<223> OTHER INFORMATION: M1-NA mutant fluorescent protein amino acid
      sequence

<400> SEQUENCE: 6

Gly Glu Gly Lys Pro Tyr Glu Gly Thr Gln Thr Met Lys Ile Lys Val
            35                  40                  45

Val Glu Gly Gly Pro Leu Pro Phe Ala Phe Asp Ile Leu Ala Thr Ser
 50                  55                  60

Phe Met Tyr Gly Ser Lys Ala Phe Ile Asn His Thr Gln Gly Ile Pro
 65                  70                  75                  80

Asp Phe Phe Lys Gln Ser Phe Pro Glu Gly Phe Thr Trp Glu Arg Ile
                 85                  90                  95

Thr Thr Tyr Glu Asp Gly Gly Val Leu Thr Ala Thr Gln Asp Thr Ser
            100                 105                 110

Phe Gln Asn Gly Cys Ile Ile Tyr Asn Val Lys Ile Asn Gly Val Asn
            115                 120                 125

Phe Pro Ser Asn Gly Pro Val Met Gln Lys Lys Thr Arg Gly Trp Glu
130                 135                 140

Ala Asn Thr Glu Met Leu Tyr Pro Ala Asp Gly Gly Leu Arg Gly His
145                 150                 155                 160

Ser Gln Met Ala Leu Lys Leu Val Gly Gly Tyr Leu His Cys Ser
            165                 170                 175

Phe Lys Thr Thr Tyr Arg Ser Lys Lys Pro Ala Lys Asn Leu Arg Met
            180                 185                 190

Pro Gly Phe His Phe Val Asp His Arg Leu Glu Arg Ile Lys Glu Ala
            195                 200                 205

Asp Lys Glu Thr Tyr Val Glu Gln His Glu Met Ala Val Ala Lys Tyr
210                 215                 220

Cys Asp Leu Pro Ser Lys Leu Gly His Ser
225                 230

<210> SEQ ID NO 7
<211> LENGTH: 705
<212> TYPE: DNA
<213> ORGANISM: Artificial sequence
<220> FEATURE:
<223> OTHER INFORMATION: M1-602 mutant fluorescent protein nucleotide
      sequence

<400> SEQUENCE: 7
atgggtgagg atagcgagct gatcaccgag aacatgcaca tgaaactgta catggagggc      60
accgtgaaca ccaccacttt caagtgcaca tccgagggcg aaggcaagcc ctacgagggc     120
acccagacca tgaagatcaa ggtggtcgag ggcggccctc tccccttcgc cttcgacatc     180
ctggctacca gcttcatgta cggcagcaaa gccttcatca accacaccca gggcatcccc     240
gacttcttta agcagtcctt ccctgagggc ttcacatggg agagaatcac cacatacgaa     300
gacgggggcg tgctgaccgc tacccaggac accagcctcc agaacggctg cctcatctac     360
aacgtcaaga tcaacggggt gaacttccca tccaacggcc ctgtgatgca agagaaaaca     420
ctcggctggg aggccagcac cgagatgctg taccccgctg acagcggcct gagaggccat     480
ggccagatgg ccctgaagct cgtgggcggg gctacctgc actgctccct caagaccaca     540
tacagatcca agaaacccgc taagaacctc aagatgcccg gcttccactt cgtggaccac     600
agactggaaa gaatcaagga ggccgacaaa gagacctacg tcgagcagca cgagatggct     660
gtggccaagt actgcgacct ccctagcaaa ctggggcaca gctga                     705

<210> SEQ ID NO 8
<211> LENGTH: 234
<212> TYPE: PRT
<213> ORGANISM: Artificial sequence
<220> FEATURE:

<223> OTHER INFORMATION: M1-602 mutant fluorescent protein amino acid
      sequence

<400> SEQUENCE: 8

Met Gly Glu Asp Ser Glu Leu Ile Thr Glu Asn Met His Met Lys Leu
1               5                   10                  15

Tyr Met Glu Gly Thr Val Asn Asn His His Phe Lys Cys Thr Ser Glu
            20                  25                  30

Gly Glu Gly Lys Pro Tyr Glu Gly Thr Gln Thr Met Lys Ile Lys Val
        35                  40                  45

Val Glu Gly Gly Pro Leu Pro Phe Ala Phe Asp Ile Leu Ala Thr Ser
50                  55                  60

Phe Met Tyr Gly Ser Lys Ala Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
        115                 120                 125

Phe Pro Ser Asn Gly Pro Val Met Gln Lys Lys Thr Leu Gly Trp Glu
130                 135                 140

Ala Ser Thr Glu Met Leu Tyr Pro Ala Asp Ser Gly Leu Arg Gly His
145                 150                 155                 160

Gly Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe His Phe Val Asp His Arg Leu Glu Arg Ile Lys Glu Ala
        195                 200                 205

Asp Lys Glu Thr Tyr Val Glu Gln His Glu Met Ala Val Ala Lys Tyr
210                 215                 220

Cys Asp Leu Pro Ser Lys Leu Gly His Ser
225                 230

<210> SEQ ID NO 9
<211> LENGTH: 705
<212> TYPE: DNA
<213> ORGANISM: Artificial sequence
<220> FEATURE:
<223> OTHER INFORMATION: M1-637 mutant fluorescent protein nucleotide
      sequence

<400> SEQUENCE: 9
atgggtgagg atagcgagct gatcaccgag aacatgcaca tgaaactgta catggagggc      60
accgtgaaca accaccactt caagtgcaca tccgagggcg aaggcaagcc ctacgagggc     120
acccagacca tgaagatcaa ggtggtcgag ggcggccctc tccccttcgc cttcgacatc     180
ctggctacca gcttcatgta cggcagcaaa gccttcatca accacaccca gggcatcccc     240
gacttcttta gcagtccctt ccctgagggc ttcacatggg agagaatcac cacatacgaa     300
gacgggggcg tgctgaccgc tacccaggac accagcctcc agaacggctg cctcatctac     360
aacgtcaaga tcaacggggt gaacttccca tccaacggcc tgtgatgca aagaaaaca       420 ctcggctggg aggccagcac cgagatgctg taccccgctg acagcggcct gagaggccat     480
agccagatgg ccctgaagct cgtgggcggg ggctacctgc actgctccct caagaccaca     540
tacagatcca agaaacccgc taagaacctc aagatgcccg gcttccactt cgtggacagg     600

```
agactggaaa gaatcaagga ggccgacaaa gagacctacg tcgagcagca cgagatggct    660
gtggccaagt actgcgacct ccctagcaaa ctggggcaca gctga                    705
```

<210> SEQ ID NO 10
<211> LENGTH: 234
<212> TYPE: PRT
<213> ORGANISM: Artificial sequence
<220> FEATURE:
<223> OTHER INFORMATION: M1-637 mutant fluorescent protein amino acid
      sequence

<400> SEQUENCE: 10

```
Met Gly Glu Asp Ser Glu Leu Ile Thr Glu Asn Met His Met Lys Leu
1               5                   10                  15

Tyr Met Glu Gly Thr Val Asn Asn His His Phe Lys Cys Thr Ser Glu
            20                  25                  30

Gly Glu Gly Lys Pro Tyr Glu Gly Thr Gln Thr Met Lys Ile Lys Val
        35                  40                  45

Val Glu Gly Gly Pro Leu Pro Phe Ala Phe Asp Ile Leu Ala Thr Ser
    50                  55                  60

Phe Met Tyr Gly Ser Lys Ala Phe Ile Asn His Thr Gln Gly Ile Pro
65                  70                  75                  80

Asp Phe Phe Lys Gln Ser Phe Pro Glu Gly Phe Thr Trp Glu Arg Ile
                85                  90                  95

Thr Thr Tyr Glu Asp Gly Gly Val Leu Thr Ala Thr Gln Asp Thr Ser
            100                 105                 110

Leu Gln Asn Gly Cys Leu Ile Tyr Asn Val Lys Ile Asn Gly Val Asn
        115                 120                 125

Phe Pro Ser Asn Gly Pro Val Met Gln Lys Lys Thr Leu Gly Trp Glu
    130                 135                 140

Ala Ser Thr Glu Met Leu Tyr Pro Ala Asp Ser Gly Leu Arg Gly His
145                 150                 155                 160

Ser Gln Met Ala Leu Lys Leu Val Gly Gly Gly Tyr Leu His Cys Ser
                165                 170                 175

Leu Lys Thr Thr Tyr Arg Ser Lys Lys Pro Ala Lys Asn Leu Lys Met
            180                 185                 190

Pro Gly Phe His Phe Val Asp Arg Arg Leu Glu Arg Ile Lys Glu Ala
        195                 200                 205

Asp Lys Glu Thr Tyr Val Glu Gln His Glu Met Ala Val Ala Lys Tyr
    210                 215                 220

Cys Asp Leu Pro Ser Lys Leu Gly His Ser
225                 230
```

<210> SEQ ID NO 11
<211> LENGTH: 693
<212> TYPE: DNA
<213> ORGANISM: Artificial sequence
<220> FEATURE:
<223> OTHER INFORMATION: M1-mono1 mutant fluorescent protein nucleotide
      sequence

<400> SEQUENCE: 11

```
atgagcgagc tgattaagga gaacatgcac atgaagctgt acatggaggg caccgtgaac    60
aaccaccact tcaagtgcac atccgagggc gaaggcaagc cctacgaggg cacccagacc   120
atgagaatca aggtggtcga gggcggccct ctccccttcg ccttcgacat cctggctacc   180
agcttcatgt acggcagcag aaccttcatc aaccacaccc agggcatccc cgacttcttt   240
```

```
aagcagtcct tccctgaggg cttcacatgg gagagagtca ccacatacga agacgggggc    300
gtgctgaccg ctacccagga caccagcctc caggacggct gcctcatcta acgtcaag      360 atcagagggg tgaacttccc atccaacggc cctgtgatgc agaagaaaac actcggctgg    420
gaggccaaca ccgagatgct gtaccccgct gacggcggcc tggaaggcag aagcgacatg    480
gccctgaagc tcgtgggcgg gggccacctg atctgcaact tcaagaccac atacagatcc    540
aagaaacccg ctaagaacct caagatgccc ggcgtctact atgtggacca cagactggaa    600
agaatcaagg aggccgacaa agagacctac gtcgagcagc acgaggtggc tgtggccaga    660
tactgcgacc tccctagcaa actggggcac aag                                 693
```

```
<210> SEQ ID NO 12
<211> LENGTH: 231
<212> TYPE: PRT
<213> ORGANISM: Artificial sequence
<220> FEATURE:
<223> OTHER INFORMATION: M1-mono1 mutant fluorescent protein amino acid
      sequence

<400> SEQUENCE: 12
```

```
Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Asn Thr
130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ile Cys Asn Phe Lys Thr
                165                 170                 175

Thr Tyr Arg Ser Lys Lys Pro Ala Lys Asn Leu Lys Met Pro Gly Val
            180                 185                 190

Tyr Tyr Val Asp His Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Lys
225                 230
```

```
<210> SEQ ID NO 13
<211> LENGTH: 702
<212> TYPE: DNA
<213> ORGANISM: Artificial sequence
<220> FEATURE:
<223> OTHER INFORMATION: nrM181-5 mutant fluorescent protein nucleotide
      sequence
```

<400> SEQUENCE: 13

```
atgagcgagc tgattaagga gaacatgcac atgaagctgt acatggaggg caccgtgaac      60
aaccaccact tcaagtgcac atccgagggc gaaggcaagc cctacgaagg cacccagacc     120
atgaaaatca aggtggtcga gggcggccct ctccccttcg ccttcgacat cctggctacc     180
agcttcatgt acggcagcaa aaccttcatc aaccacaccc agggcatccc cgacttcttt     240
aagcagtcct tccctgaggg cttcacatgg gagagagtca ccacatacga agacgggggc     300
gtgctgaccg ctacccagga caccagcctc caggacggct gcctcatcta caacgtcaag     360
atcagagggg tgaacttccc atccaacggc cctgtgatgc agaagaaaac actcggctgg     420
gaggcccaca ccgagatgct gtaccccgct gacggcggcc tggaaggcag aagcgacatg     480
gccctgaagc tcgtgggcgg gggccacctg atcgccaact tcaagaccac atacagatcc     540
aagaaacccg ctaagaacct caagatgccc ggcgtctact atgtggacca cagactggaa     600
agaatcaagg aggccgacaa agagacctac gtcgagcagc acgagatggc tgtggccaaa     660
tactgcgacc tccctagcaa actggggcac aagcttaatt ag                         702
```

<210> SEQ ID NO 14
<211> LENGTH: 233
<212> TYPE: PRT
<213> ORGANISM: Artificial sequence
<220> FEATURE:
<223> OTHER INFORMATION: nrM181-5 mutant fluorescent protein amino acid
sequence

<400> SEQUENCE: 14

```
Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Lys Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala His Thr
    130                 135                 140

Glu Met Leu Tyr Pro Ala Asp Gly Gly Leu Glu Gly Arg Ser Asp Met
145                 150                 155                 160

Ala Leu Lys Leu Val Gly Gly Gly His Leu Ile Ala Asn Phe Lys Thr
                165                 170                 175

Thr Tyr Arg Ser Lys Lys Pro Ala Lys Asn Leu Lys Met Pro Gly Val
            180                 185                 190

Tyr Tyr Val Asp His Arg Leu Glu Arg Ile Lys Glu Ala Asp Lys Glu
        195                 200                 205

Thr Tyr Val Glu Gln His Glu Met Ala Val Ala Lys Tyr Cys Asp Leu
    210                 215                 220
```

Pro Ser Lys Leu Gly His Lys Leu Asn
225                 230

<210> SEQ ID NO 15
<211> LENGTH: 702
<212> TYPE: DNA
<213> ORGANISM: Artificial sequence
<220> FEATURE:
<223> OTHER INFORMATION: Cyan-2-1 mutant fluorescent protein nucleotide
      sequence

<400> SEQUENCE: 15

```
atgagcgagc tgattaagga gaacatgcac atgaagctgt acatggaggg caccgtgaac      60
aaccaccact tcaagtgcac atccgagggc gaaggcaagc cctacggagg cacccagacc     120
atgagaatca aggtggtcga gggcggccct ctccccgtcg ccttcgacat cctggctacc     180
agcttcatgt acggcagcag aaccttcatc aaccacaccc agggcatccc cgacttcttt     240
aagcagtcct tccctgaggg cttcacatgg gagagagtca ccacatacga agacgggggc     300
gtgctgaccg ctacccagga caccagcctc caggacggct gcctcatcta caacgtcaag     360
atcagagggg tgaacttccc atccaacggc cctgtgatgc agaagaaaac actcggctgg     420
gaggccttca ccgagatgct gtaccccgct gacggcggcc tggaaggcag aagcgacatg     480
gccctgaagc tcgtgggcgg gggccacctg atctgcaact tcaagaccac atacagatcc     540
aagaaacccg ctaagaacct caagatgccc ggcgtctact atgtggacta cagactggaa     600
agaatcaagg aggccgacaa agagacctac gtcgagcagc acgaggtggc tgtggccaga     660
tactgcgacc tccctagcaa actggggcac aagcttaatt ag                        702
```

<210> SEQ ID NO 16
<211> LENGTH: 233
<212> TYPE: PRT
<213> ORGANISM: Artificial sequence
<220> FEATURE:
<223> OTHER INFORMATION: Cyan-2-1 mutant fluorescent protein amino acid
      sequence

<400> SEQUENCE: 16

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Gly Gly Thr Gln Thr Met Arg Ile Lys Val Val Glu Gly
        35                  40                  45

Gly Pro Leu Pro Val Ala Phe Asp Ile Leu Ala Thr Ser Phe Met Tyr
    50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Phe Thr
    130                 135                 140

Glu Met Leu Tyr Pro Ala Asp Gly Gly Leu Glu Gly Arg Ser Asp Met
145                 150                 155                 160

Ala Leu Lys Leu Val Gly Gly Gly His Leu Ile Cys Asn Phe Lys Thr

-continued

```
                165                 170                 175
Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230

<210> SEQ ID NO 17
<211> LENGTH: 4
<212> TYPE: PRT
<213> ORGANISM: Artificial sequence
<220> FEATURE:
<223> OTHER INFORMATION: amino acid composition for N-terminus of
      non-aggregating fluorescent proteins

<400> SEQUENCE: 17

Met Gly Glu Tyr
1

<210> SEQ ID NO 18
<211> LENGTH: 4
<212> TYPE: PRT
<213> ORGANISM: Artificial sequence
<220> FEATURE:
<223> OTHER INFORMATION: amino acid composition for N-terminus of
      non-aggregating fluorescent proteins

<400> SEQUENCE: 18

Met Gly Glu Asp
1
```

FLUORESCENT PROTEINS AND METHODS FOR USING SAME

CROSS-REFERENCE TO RELATED APPLICATIONS

This application is a divisional of co-pending U.S. patent application Ser. No. 12/619,488, filed Nov. 16, 2009, which is a divisional of U.S. patent application Ser. No. 11/651,728, filed Jan. 9, 2007 (now issued as U.S. Pat. No. 7,638,615), which claims benefit of U.S. Provisional Patent Application Ser. No. 60/761,807, filed Jan. 25, 2006. Each of the aforementioned related patent application is herein incorporated by reference in its entirety.

BACKGROUND OF THE INVENTION

1. Field of the Invention

This invention relates generally to the field of biology and chemistry. More particularly, the invention is directed to fluorescent proteins.

2. Description of the Related Art

Fluorescent proteins including Green Fluorescent Protein (GFP), its mutants, and homologs are widely known today due to their intensive use as in vivo fluorescent markers in biomedical sciences as discussed in detail by Lippincott-Schwartz and Patterson in Science (2003) 300(5616):87-91.

Fluorescent proteins are proteins that exhibit fluorescence upon irradiation with light of the appropriate excitation wavelength. The fluorescent characteristic of these proteins is one that arises from the interaction of two or more amino acid residues of the protein, and not from a single amino acid residue.

The GFP from hydromedusa *Aequorea aequorea* (synonym *A. victoria*), described by Johnson et al. in J Cell Comp Physiol. (1962), 60:85-104, was found as a part of bioluminescent system of the jellyfish where GFP played role of a secondary emitter transforming blue light from photoprotein aequorin into green light. cDNA encoding *A. victoria* GFP was cloned by Prasher et al. (Gene (1992), 111(2):229-33). It turned out that this gene can be heterologously expressed in practically any organism due to unique ability of GFP to form a fluorophore by itself (Chalfie et al., Science 263 (1994), 802-805). This finding opens broad perspectives for use of GFP in cell biology as a genetically encoded fluorescent label.

The GFP was applied for wide range of applications including the study of gene expression and protein localization (Chalfie et al., Science 263 (1994), 802-805, and Heim et al. in Proc. Nat. Acad. Sci. (1994), 91: 12501-12504), as a tool for visualizing subcellular organelles in cells (Rizzuto et al., Curr. Biology (1995), 5: 635-642), for the visualization of protein transport along the secretory pathway (Kaether and Gerdes, FEBS Letters (1995), 369: 267-271).

A great deal of research is being performed to improve the properties of GFP and to produce GFP reagents useful and optimized for a variety of research purposes. New versions of GFP have been developed, such as a "humanized" GFP DNA, the protein product of which has increased synthesis in mammalian cells (Haas, et al., Current Biology (1996), 6: 315-324; Yang, et al., Nucleic Acids Research (1996), 24: 4592-4593). One such humanized protein is the "enhanced green fluorescent protein" (EGFP) mutant variant of GFP having two amino acid substitutions: F64L and S65T (Heim et al., Nature 373 (1995), 663-664). Other mutations to GFP have resulted in blue-, cyan- and yellow-green light emitting versions.

Despite the great utility of GFP, however, other fluorescent proteins with properties similar to or different from GFP would be useful in the art. In particular, benefits of novel fluorescent proteins include possibilities based on new spectra and better suitability for larger excitation. In 1999, GFP homologues were cloned from non-bioluminescent *Anthozoa* species (Matz et al., Nature Biotechnol. (1999), 17: 969-973). This discovery demonstrated that these proteins are not a necessary component of bioluminescence machinery. *Anthozoa*-derived GFP-like proteins showed great spectral diversity including cyan, green, yellow, red fluorescent proteins and purple-blue non-fluorescent chromoproteins (CPs) (Matz et al., Bioessays (2002), 24(10):953-959). Afterwards, cDNA of GFP-like proteins were cloned from several Hydroid jellyfishes and Copepods (Shagin et al., Mol Biol Evol. (2004), 21(5):841-850). GFP-like proteins already revealed over 120 fluorescent and colored GFP homologues. Similarity of these proteins to GFP ranges from 80-90% to less than 25% identity in amino-acid sequence.

The crystal structures of wild-type GFP and the GFP S65T mutant have been solved and reveal that the GFP tertiary structure resembles a barrel (Ormo et al., 1996, Science 273: 1392-1395; Yang, et al., 1996, Nature Biotech 14: 1246-1251). The barrel consists of beta sheets in a compact antiparallel structure, within which an alpha helix containing the chromophore is contained. The chromophore was confirmed to be formed by oxidative cyclization of three consecutive amino-acid residues, as was inferred from earlier biochemical studies (Cody et al., Biochemistry (1993) 32, 1212-1218). All GFP-like proteins tested share the same beta-can fold as GFP (Ormo et al. Science (1996) 273: 1392-1395; Wall et al. Nat Struct Biol (2000), 7: 1133-1138; Yarbrough et al. Proc Natl Acad Sci USA (2001) 98: 462-467; Prescott et al. Structure (Camb) (2003), 11: 275-284; Petersen et al. J Biol Chem (2003), 278: 44626-44631; Wilmann et al. J Biol Chem (2005), 280: 2401-2404; Remington et al. Biochemistry (2005), 44, 202-212; Quillin et al. Biochemistry (2005), 44: 5774-5787).

The utility of fluorescent proteins as a tool in molecular biology has prompted the search for other fluorescent proteins with different and improved properties, as compared to known fluorescent proteins. Thus, it is an object to provide novel fluorescent proteins that exhibit properties not currently available in the known fluorescent proteins, as well as DNAs encoding them.

SUMMARY OF THE INVENTION

The present invention provides isolated nucleic acid molecules encoding a novel fluorescent protein from *Entacmaea quadricolor* (EqFP578) and functional mutants thereof, i.e. EqFP578—related proteins. In certain embodiments, a nucleic acid of the present invention is isolated from *Entacmaea quadricolor*. In other embodiments, a nucleic acid of the present invention is genetically engineered.

In certain embodiments, isolated nucleic acids of the present invention encode wild type *Entacmaea quadricolor* fluorescent protein of SEQ ID NO: 02 (EqFP578). An exemplary nucleic acid sequence is shown in SEQ ID NO: 01.

In other embodiments, an isolated nucleic acid molecule is provided, which has a sequence specifically hybridizing with preselected portions or all of the complementary strand of SEQ ID NO: 01.

In certain embodiments, nucleic acids of the present invention encode a fluorescent protein that comprises an amino acid sequence that is substantially the same as or identical to the sequence of EqFP578 protein (SEQ ID NO: 02). Accordingly, isolated nucleic acid sequences encoding natural allelic variants of SEQ ID NO: 01 are also contemplated to be within the scope of the present invention.

In certain embodiments, the nucleic acids provided encode functional mutants of EqFP578 that have substantially similar or altered biochemical and/or spectral properties compared to wild type EqFP578.

In certain embodiments, isolated nucleic acids of the present invention encode a mutant fluorescent protein that comprises an amino acid sequence substantially the same as the sequence of EqFP578 (SEQ ID NO: 02) and differs from EqFP578 (SEQ ID NO: 02) by at least one amino acid substitution.

In preferred embodiments, said amino acid substitution is selected from the group consisting of R32G and S131 P; said mutant fluorescent protein has improved folding at 37° C. than EqFP578. In preferred embodiments, said mutant comprises both substitutions.

In preferred embodiments, said mutant further comprises other folding mutations, e.g., selected from the group consisting of E36G, K42R, F53V, K67R, T68A, L79F, I93V, F110L, N112D, I115L, R138L, G152S, H157R, Y169H, H171I, C172A, F174L, K188R, H193Y, M216V, K220R, and R231K. These mutations enhance protein folding and chromophore maturation rate, resulting in faster generation of a fluorescent signal in vivo.

In other preferred embodiments, the isolated nucleic acids of the present invention encode an engineered fluorescent protein that has modified N- and\or C-terminal part(s) outside from the chromophore domain of EqFP578, wherein said protein possesses reduced aggregation capacity compared to wild type EqFP578. In a preferred embodiment, the modified N-terminus comprises a K6T substitution and C-terminal R231S substitution. In some embodiments, the modified N-terminus also comprises an additional N-terminal amino acid sequence selected from the group consisting of MGEY and MGED.

In certain embodiments, the isolated nucleic acids of the present invention encode an engineered functional fluorescent protein that comprises at least one substitution selected from the group consisting of R155E, Q159D, S173N, F192V, F194Y, wherein said functional fluorescent protein has reduced oligomerization capacity compared to wild type EqFP578. In a preferred embodiment, said functional fluorescent protein also comprises a N122R substitution that further reduces the protein's tendency to oligomerize. In a preferred embodiment, said functional fluorescent protein comprises all noted substitutions and further comprises one or more substitutions selected from the group consisting of E36G, K42R, F53V, K67R, T68A, L79F, I93V, F110L, N112D, I115L, R138L, G152S, H157R, Y169H, H171I, C172A, F174L, K188R, H193Y, M216V, K220R, and R231K, wherein those substitutions enhance protein folding and fluorescence intensity in vivo.

In some embodiments, the isolated nucleic acids of the present invention encode an engineered functional fluorescent protein that comprises at least one substitution selected from the group consisting of H197R, S158G, N143S, N143H, N143F and N143Y, wherein said functional fluorescent protein has altered excitation and emission spectra than the corresponding wild type protein.

Exemplary nucleic acid molecules of the invention that encode engineered functional mutants of EqFP578 include SEQ ID NO: 3, 5, 7, 9, 11, 13, and 15 or encode SEQ ID NO: 4, 6, 8, 10, 12, 14, and 16.

Nucleic acid molecules that differ from the nucleic acid sequences of the present due to the degeneracy of genetic code, or hybridize thereto, are also within the scope of the present invention.

In yet other embodiments there are provided vectors comprising a nucleic acid of the present invention. In addition, the present invention provides expression cassettes comprising a nucleic acid of the present invention and regulatory elements necessary for expression of the nucleic acid in the desired host-cell. Additionally, host-cells, stable cell lines, transgenic animals and transgenic plants comprising nucleic acids, vectors or expression cassettes of the present invention are provided.

In yet other embodiments there are provided functional fluorescent proteins of the invention that are encoded by the nucleic acids noted above.

In certain embodiments, a functional fluorescent protein of the present invention comprises an amino acid sequence that is substantially same as or identical to the sequence of the wild type *Entacmaea quadricolor* fluorescent protein of SEQ ID NO: 02 (EqFP578). The proteins of interest includes wild type EqFP578 and mutants thereof, that has substantially similar or altered biochemical and/or spectral properties compared to wild type EqFP578

In preferred embodiments, said amino acid substitution is selected from the group consisting of R32G and S131P, and said functional fluorescent protein has improved folding at 37° C. compared to EqFP578. In preferred embodiments, said mutant comprises both substitutions.

In some embodiments, said mutant further comprises other folding mutations, e.g., selected from the group consisting of E36G, K42R, F53V, K67R, T68A, L79F, I93V, F110L, N112D, I115L, R138L, G152S, H157R, Y169H, H171I, C172A, F174L, K188R, H193Y, M216V, K220R, and R231K. These mutations enhance protein folding and chromophore maturation rate, resulting in faster generation of a fluorescent signal in vivo.

In other preferred embodiments, the engineered fluorescent protein has modified N- and \or C-terminal part(s), wherein said protein possesses reduced aggregation capacity compared to wild type EqFP578. In a preferred embodiment, the modified N-terminus comprises a K6T substitution and C-terminal R231S substitution. In some embodiments, the modified N-terminus also comprises an additional N-terminal amino acid sequence selected from the group consisting of MGEY and MGED (SEQ ID NOs: 17 and 18, respectively).

In certain embodiments, the engineered functional fluorescent protein of the present invention comprises at least one substitution selected from the group consisting of R155E, Q159D, S173N, and F192V, wherein said functional fluorescent protein has reduced oligomerization capacity compared to wild type EqFP578. In a preferred embodiment, said functional fluorescent protein also comprises a N122R substitution that further reduces oligomerization capacity of the protein. In a preferred embodiment, said functional fluorescent protein comprises all noted substitutions and further comprises one or more substitutions selected from the group consisting of E36G, K42R, F53V, K67R, T68A, L79F, I93V, F110L, N112D, I115L, R138L, G152S, H157R, Y169H, H171I, C172A, F174L, K188R, H193Y, M216V, K220R, and R231K, wherein those substitutions enhance protein folding and fluorescence intensity in vivo.

In some embodiments, the engineered functional fluorescent protein of the present invention comprises at least one substitution selected from the group consisting of H197R, S158G, N143S, N143H, N143F and N143Y, wherein said functional fluorescent protein has altered excitation and emission spectra compared to wild type protein.

Exemplary fluorescent proteins of interest include SEQ ID NO: 02, 4, 6, 8, 10, 12, 14, and 16.

Additionally, kits comprising nucleic acids or vectors or expression cassettes harboring said nucleic acids, or proteins of the present invention are provided.

In addition, antibodies specifically binding to the proteins of the present invention or to fragments thereof are provided.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 shows a multiple sequence alignment of wild type EqFP578 and mutants thereof.

DETAILED DESCRIPTION

Figure 2:
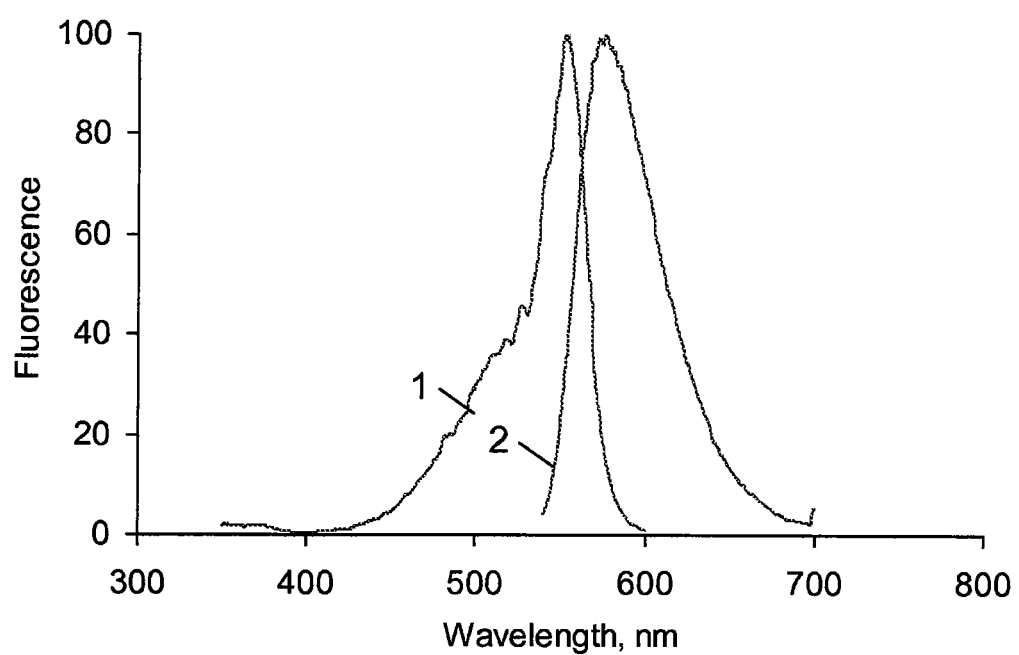
FIG. 2 illustrates the excitation (line 1) and emission (line 2) fluorescent spectra for wild type EqFP578.

As summarized above, the present invention is directed to nucleic acid molecules encoding *Entacmaea quadricolor* fluorescent protein EqFP578 and mutants thereof as well as proteins encoded by these nucleic acids. The nucleic acid molecules of interest are isolated from *Entacmaea quadricolor* or genetically engineered. The proteins of interest include fluorescent proteins having amino acid compositions shown in SEQ ID NO: 2, 4, 6, 8, 10, 12, 14, and 16. Also of interest are proteins that are substantially similar to, or mutants of, the above-referenced specific proteins. Also provided are host-cells, stable cell lines and transgenic organisms comprising the above-referenced nucleic acid molecules. In addition antibodies specific to the proteins of the invention are provided.

The subject protein and nucleic acid compositions find use in a variety of different applications and methods, particularly cell, cell organelle or protein labeling applications. Also the subject protein and nucleic acid compositions find use in the methods of testing promoter activities under various conditions. Finally, kits for use in such methods and applications are provided.

DEFINITIONS

Various terms relating to the biological molecules of the present invention are used herein above and also throughout the specifications and claims.

As used herein the term "fluorescent protein" means a protein that is fluorescent; e.g., it may exhibit low, medium or intense fluorescence upon irradiation with light of the appropriate excitation wavelength. The fluorescent characteristic of fluorescent protein is one that arises from the chromophore wherein the chromophore results from autocatalytic cyclization of two or more amino acid residues in the polypeptide backbone. As such, the fluorescent proteins of the present invention do not include proteins that exhibit fluorescence only from residues that act by themselves as intrinsic fluors, i.e., tryptophan, tyrosine and phenylalanine.

As used herein, the term "GFP" refers to the green fluorescent protein from *Aequorea victoria*, including prior art versions of GFP engineered to provide greater fluorescence or fluoresce at different wavelengths. The sequence of *Aequorea victoria* GFP has been disclosed by Prasher et al. (1992, Gene 111: 229-33).

As used herein, the term "EGFP" refers to a mutant variant of GFP having two amino acid substitutions: F64L and S65T (Heim et al., 1995, Nature 373:663-664).

The term "humanized" refers to changes made to the fluorescent protein nucleic acid sequence to optimize codon usage for expression of the protein in mammalian cells (Yang et al., 1996, Nucleic Acids Research 24:4592-4593).

As used herein, the term "EqFP578" refers to the nucleic acid and protein of the wild type *Entacmaea quadricolor* fluorescent protein that has nucleotide and amino acid sequences shown in SEQ ID NOs: 1 and 2, respectively.

As used herein the term "isolated" means a molecule or a cell that is an environment different from that in which the molecule or the cell naturally occurs.

As used herein the terms "mutant" or "derivatives" refer to protein disclosed in the present invention, in which one or more amino acids are added and/or substituted and/or deleted and/or inserted at the N-terminus, and/or the C-terminus, and/or within the native amino acid sequences of the proteins of the present invention. As used herein the term "mutant" refers to a nucleic acid molecule that encodes a mutant protein. Moreover, the term "mutant" refers to any shorter or longer version of the protein or nucleic acid herein.

As used herein, "homologue or homology" is a term used in the art to describe the relatedness of a nucleotide or peptide sequence to another nucleotide or peptide sequence, which is determined by the degree of identity and/or similarity between said sequences compared.

As used herein, an amino acid sequence or a nucleotide sequence is "substantially the same as" or "substantially similar to" a reference sequence if the amino acid sequence or nucleotide sequence has at least 85% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are also substantially similar. For purposes of this invention, the length of comparison sequences of fluorescent protein will generally be at least 160 amino acids, preferably at least 200 amino acids. For nucleic acids, the length of comparison sequences will generally be at least 480 nucleotides, preferably at least 600 nucleotides.

Sequence identity is calculated based on a reference sequence. Algorithms for sequence analysis are known in the art, such as BLAST, described in Altschul et al., J. Mol. Biol., 215, pp. 403-10 (1990). For purposes of this invention comparisons of nucleic acid or amino acid sequences are performed with Blast software provided by the National Center for Biotechnology Information using a gapped alignment with default parameters, may be used to determine the level of identity and similarity between nucleic acid sequences and amino acid sequences.

As used herein, the term "related fluorescent protein" refers to a fluorescent protein that has a substantially same amino acid sequence when compared to a reference fluorescent protein. In general, a related fluorescent protein, when compared to the reference fluorescent protein sequence, has a contiguous sequence of at least about 160 amino acids that shares at least 85% sequence identity with the reference fluorescent protein.

As used herein the term "EqFP578-related protein" refers to the wild type protein EqFP578 of SEQ ID NO: 2 and functional mutants thereof, e.g., that have amino acid sequences shown in SEQ ID NOs: 2, 4, 6, 8, 10, 12, 14, and 16. As used herein the term "EqFP578-related nucleic acid" refers to a nucleic acid that encodes an EqFP578-related protein (e.g. SEQ ID NOs: 1, 3, 5, 7, 9, 11, 13, and 15). As used herein EqFP578-related protein comprises an amino acid sequence that is substantially the same as or identical to the sequence of EqFP578 (SEQ ID NO: 02). The terms "EqFP578-related protein" and "EqFP578-related nucleic acid" also refers to shorter or longer variants of EqFP578 or its mutants and nucleic acids encoding them.

As used herein, the term "functional" implies that the nucleic or amino acid sequence is functional for the recited assay or purpose. The term "functional" when used to describe fluorescent proteins means that the protein has useful excitation and emission spectra (i.e., possesses detectable fluorescence).

As used herein, "biochemical property" refers to the protein folding and maturation rate, half life before degradation, aggregation capacity, oligomerization capacity, pH or temperature stability and optimum, and other like properties.

As used herein, "fluorescent property" or "spectral property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type EqFP578 and the mutant form is useful. A measurable difference can be determined as the amount of any quantitative fluorescent property, e.g., the amount of fluorescence at a particular wavelength, or the integral of fluorescence over the emission spectrum.

As used herein, "maturation rate" or "maturation speed" refers to the rate of mature fluorescent protein formation (i.e., fluorescent protein capable of producing fluorescence) after translation. Maturation rate can be characterized with a half-time of maturation. It has been discovered that maturation of fluorescent protein includes two steps: (i) Protein folding that means formation of a protein beta-barrel with a central alpha-helix containing amino acids that will form a chromophore. This step is commonly characterized with a rate constant of about $10^{(-2)}s^{(-1)}$ or half-time from several seconds to tens of seconds; (ii) Chromophore maturation, that is protein backbone cyclization and dehydration. This stage is commonly characterized with a rate constant of about $10^{(-4)}s^{(-1)}$ or half-time about several minutes. Therefore, this slower step is the limiting in green fluorescent proteins maturation (Reid B G, Flynn G C. Biochemistry. 1997 V. 36(22), PP. 6786-6791).

As used herein, "aggregation" refers to the tendency or capacity of an expressed protein to form insoluble precipitates (aggregates). "Aggregation" should be distinguished from "oligomerization". In particular, mutations that reduce aggregation, e.g., increase the solubility of the protein, do not necessarily reduce oligomerization (i.e., convert tetramers to dimers or monomers or dimers to monomers).

As used herein, "oligomerization" refers to the tendency or capacity of an expressed protein to form complexes (oligomers) due to specific interaction of two or more polypeptides. Said specific interaction occurs under specified conditions, for example, physiologic conditions and is relatively stable under these conditions. Reference to a "capacity" of proteins to oligomerize indicates that the proteins can form dimers, trimers, tetramers, or the like under specified conditions. Generally, fluorescent proteins have a capacity to oligomerize under physiologic conditions although, as disclosed herein, fluorescent proteins also can oligomerize, for example, under pH conditions other than physiologic conditions. The conditions under which fluorescent proteins oligomerize or have a tendency to oligomerize can be determined using well known methods such as gel-filtration or otherwise known in the art.

The term "operatively linked" or "operably linked" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein of the present invention can be fused to a fusion partner of interest. In this case, the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention.

As used herein the term "specifically hybridize" refers to the association between two single-stranded nucleic acid molecules of sufficiently complementary sequence to permit such hybridization under pre-determined conditions generally used in the art (sometimes termed "substantially complementary").

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

As used herein, numeration of amino acid residues and substitutions correspond to the numeration of amino acid residues in the wild type EqFP578 sequence (SEQ ID NO: 2). For mutant proteins, the position of the amino acid residue or substitution should be determined using protein alignment (FIG. 1).

Nucleic Acid Molecules

The present invention provides nucleic acid molecules encoding a fluorescent protein EqFP578 having an amino acid sequence SEQ ID NO: 2 and mutants thereof. Nucleic acid molecules encoding shorter or longer variants of the EqFP578 or its mutants are also in the scope of the invention.

Specific nucleic acid molecules of interest include nucleic acid molecules that encode the following fluorescent proteins: *Entacmaea quadricolor* red fluorescent protein having the sequence of SEQ ID No: 2; and mutants thereof with optimized useful properties: protein folding at 37° C., decreased aggregation and/or oligomerization capacity, and altered spectral characteristics. Amino acid sequences for these mutants are shown in SEQ ID Nos: 4, 6, 8, 10, 12, 14, and 16. Exemplary specific mutant nucleic acids of the invention are shown in SEQ ID Nos: 3, 5, 7, 9, 11, 13, and 15.

Each of these particular types of nucleic acid molecules of interest is discussed below in more detail in the experimental part, infra.

A nucleic acid molecule as used herein is a DNA molecule, such as a genomic DNA molecule or a cDNA molecule, or an RNA molecule, such as a mRNA molecule. The term "cDNA" as used herein is intended to include nucleic acids that share the arrangement of sequence elements found in native mature mRNA species, where sequence elements are exons and 5' and 3' non-coding regions.

Nucleic acid molecules encoding the fluorescent proteins of the invention may be synthesized from appropriate nucleotide triphosphates or isolated from biological sources. Both methods utilize protocols well known in the art. For example, the availability of amino acid sequence information (e.g. SEQ ID NO: 2, 4, 6, 8, 10, 12, 14, or 16) or nucleic acid sequence information (e.g. SEQ ID NO: 3, 5, 7, 9, 11, 13, or 15) enables preparation of isolated nucleic acid molecules of the invention by oligonucleotide synthesis. In the case of amino acid sequence information, a number of nucleic acids that differ from each other due to degenerate code may be synthesized. The methods to select codon usage variants for desired hosts are well known in the art.

Synthetic oligonucleotides may be prepared by the phosphoramidite method, and the resultant constructs may be purified according to methods known in the art, such as high performance liquid chromatography (HPLC) or other methods as described in, for example, Sambrook et al., Molecular Cloning: A Laboratory Manual, $2^{nd}$ Ed., (1989) Cold Spring Harbor Press, Cold Spring Harbor, N.Y., and under regulations described in, e.g., United States Dept. of HHS, National Institute of Health (NIH) Guidelines for Recombinant DNA Research. Long, double-stranded DNA molecules of the present invention may be synthesized by following stages: several smaller segments of appropriate complementarity can be synthesized that comprise appropriate cohesive termini for attachment of an adjacent segment. Adjacent segments may be linked using DNA ligase or PCR-based methods.

Nucleic acid molecules encoding the fluorescent proteins of the invention may be also cloned from biological sources from phylum Cnidaria, preferably from class Anthozoa, more preferably from subclass Zoantharia, more preferably from order Actiniaria and even more preferably from family Actimidae, e.g., from *Entacmaea quadricolor*.

In certain embodiments, a nucleic acid molecule of the invention is a DNA (or cDNA) molecule comprising an open reading frame that encodes the *Entacmaea quadricolor* fluorescent protein of the invention and is capable, under appropriate conditions (e.g., cell physiological conditions), of being expressed as a fluorescent protein according to the invention. The invention also encompasses nucleic acids that are homologous, substantially the same as, identical to, or derived from the nucleic acids encoding proteins of the present invention. The subject nucleic acids are present in an environment other than their natural environment; e.g., they are isolated, present in enriched amounts, or are present or expressed in vitro or in a cell or organism other than their naturally occurring environment.

Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

A nucleic acid encoding an EqFP578-related polypeptide which is an amino acid sequence mutant, variant, derivative or allele of the sequence shown in SEQ ID NO: 2 is further provided by the present invention. A nucleic acid encoding such polypeptide may show greater than 60% homology with the coding sequence shown in SEQ ID NO: 1, greater than about 70% homology, greater than about 80% homology, greater than about 90% homology or greater than about 95% homology.

A nucleic acid encoding such polypeptide or fragments thereof may be isolated by any of a number of known methods. A fragment of a cDNA of the present invention may be used as a hybridization probe against a cDNA library from a target organism using high stringency conditions. The probe may be a large fragment, or one or more short degenerate primers. Nucleic acids having sequence similarity are detected by hybridization under high stringency conditions, for example 50 degrees C. or above (e.g., 60 degrees C. or 65 degrees C.), 50% formamide, 0.1×SSC (15 mM sodium chloride/1.5 mM sodium citrate), 0.1% SDS. Nucleic acids having a region of substantial identity to the provided sequences, e.g., allelic variants, genetically-altered versions of the nucleic acid, etc., bind to the provided sequences under high stringency hybridization conditions. By using probes, particularly labeled probes of DNA sequences, one can isolate related nucleic acids.

Mutant or derivative nucleic acids can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof. In some embodiments, fluorescent proteins encoded by mutant or derived nucleic acids have the same fluorescent or biochemical properties as the wild type fluorescent protein. In other embodiments, mutant or derived nucleic acids encode fluorescent proteins with altered properties.

In addition, degenerate variants of the nucleic acids that encode the proteins of the present invention are also provided. Degenerate variants of nucleic acids comprise replacements of the codons of the nucleic acid with other codons encoding the same amino acids. In particular, degenerate variants of the nucleic acids are generated to increase its expression in a host cell. In this embodiment, codons of the nucleic acid that are non-preferred or less preferred in genes in the host cell are replaced with the codons over-represented in coding sequences in genes in the host cell, wherein said replaced codons encode the same amino acid. Humanized versions of the nucleic acids of the present invention are of particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins, the disclosure of which is herein incorporated by reference. Examples of degenerate variants of interest are described in more detail in the experimental part, infra.

Nucleic acids encoding shorter or longer variants of the EqFP578 or mutants thereof are also in the scope of the invention. As used herein, these protein variants comprise amino acid sequences of EqFP578-related protein with modified C-, N-, or both termini. In longer variants, the C- or N-terminus of the protein may comprise additional amino acid residues. In shorter variants one or more (usually up to 8, more usually up to 7 and preferably up to 5) amino acid residues should be eliminated from the sequence or replaced by any other amino acid residues. Such modifications do not substantially alter fluorescent properties of the proteins, but can facilitate protein folding in host cells, decrease aggregation capacity or modulate other biochemical properties of the proteins, for example, half life before degradation. In some embodiments, these modifications do not modify biochemical properties of the protein. All types of modifications and mutations noted above are performed at the nucleic acid level.

The nucleic acid molecules of the invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, or about 200 amino acids up to the full length protein.

The subject nucleic acids may be isolated and obtained in substantially purified form. Substantially purified form means that the nucleic acids are at least about 50% pure, usually at least about 90% pure and are typically "recombinant", i.e., flanked by one or more nucleotides with which it is not normally associated on a naturally-occurring chromosome in its natural host organism.

Also provided are nucleic acids that encode fusion proteins comprising a protein of the present invention, or fragments thereof that are discussed in more detail below.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject chromogenic or fluorescent proteins or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operatively linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g., co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus oocytes*, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

Proteins

Also provided by the subject invention are fluorescent proteins, derivates, and mutants thereof including full-length proteins, as well as portions or fragments thereof. Also provided are variants of the naturally occurring *Entacmaea quadricolor* protein (SEQ ID No:2), where such variants are homologous or substantially the same as the naturally occurring protein, and mutants of the naturally occurring proteins, as described in greater detail below.

The subject proteins are fluorescent, i.e., they possess detectable fluorescence. In many embodiments, the subject proteins possess red or far-red fluorescence, i.e., they have an absorbance maximum ranging from about 450 nm to 700 nm, usually from about 470 nm to 650 nm and more usually from about 500 to 600 nm, e.g., from 550 to 595 nm; while the emission spectra of the subject proteins typically ranges from about 530 to 700 nm, usually from about 550 nm to 670 nm and more usually from about 560 to 650 nm, e.g., from 574 to 637 nm. In other embodiments, the subject proteins have an absorbance maximum ranging from about 350 to 500 nm, usually from about 370 nm to 450 nm and more usually from about 390 to 420 nm, e.g., at 400 nm; while the emission spectra of the subject proteins typically ranges from about 400 to 530 nm, usually from about 420 nm to 510 nm, e.g. about 470 nm.

The subject proteins generally have a maximum extinction coefficient that ranges from about 30,000 to 150,000 and usually from about 60,000 to 120,000, e.g., 90,000 to 120,000.

The subject proteins typically range in length from about 150 to 300 amino acids and usually from about 200 to 300 amino acid residues, and generally have a molecular weight ranging from about 15 to 35 kDa, usually from about 17.5 to 32.5 kDa.

In certain embodiments, the subject proteins are bright, whereby bright means that fluorescent proteins can be detected by common methods (e.g., visual screening, spectrophotometry, spectrofluorometry, fluorescent microscopy, by FACS machines, etc.) Fluorescence brightness of a particular fluorescent protein is determined by its quantum yield multiplied by maximal extinction coefficient and divided by 1000. In many embodiments, the subject proteins have fluorescence brightness from about 10 to 90, usually from about 40 to 80, and more usually from about 50 to 75.

In some embodiments, the subject proteins are photoactivatable photoquenchable or photoswitchable, i.e., they exchange fluorescent properties under irradiation of light of the certain wavelength and intensity. For example, they can posses blue fluorescence (with emission at about 440-500 nm) before irradiation and red fluorescence (with emission at about 540-650 nm) after irradiation with UV-violet light (e.g. about 400 nm). In some embodiments said proteins can posses red fluorescence before irradiation that is reduced upon light irradiation (e.g. UV- or blue light). In another embodiment, said proteins can be non-fluorescent (chromogenic) before but fluorescent after irradiation with UV- or blue light.

In certain embodiments, the subject proteins fold rapidly following expression in the host cell. By rapidly folding is meant that the proteins achieve their tertiary structure that gives rise to their fluorescent quality in a short period of time. In these embodiments, the half time of proteins folding generally does not exceed about 48 hrs, usually does not exceed about 24 hrs and more usually does not exceed about 12 hrs (for example the half time of proteins folding can be 3 hrs).

Specific proteins of interest include red fluorescent protein EqFP578 from *Entacmaea quadricolor* from the phylum Cnidaria, preferably from class Anthozoa, more preferably from subclass Zoantharia, more preferably from order Actiniaria and even more preferably from family Actimidae (SEQ ID No: 2); and functional mutants thereof.

Mutants may retain biological properties of the wild type (e.g., naturally occurring) proteins, or may have biological properties which differ from the wild type proteins. The term "biological property" of the proteins of the present invention refers to, but is not limited to, spectral properties, such as absorbance maximum, emission maximum, maximum extinction coefficient, brightness (e.g., as compared to the reference protein), and the like; biochemical properties, such as in vivo and/or in vitro stability (e.g., half-life); maturation speed, aggregation tendency and oligomerization tendency and other such properties (as compared to the reference protein). Mutations include single amino acid changes, deletions or insertions of one or more amino acids, N-terminal truncations or extensions, C-terminal truncations or extensions and the like.

Mutants can be generated using standard techniques of molecular biology as described in detail in the section "Nucleic acid molecules" above. Given the guidance provided in the Examples, and using standard techniques, those skilled in the art can readily generate a wide variety of additional mutants and test whether a biological (e.g., biochemical, spectral, etc.) property has been altered. For example, fluorescence intensity can be measured using a spectrophotometer at various excitation wavelengths.

Proteins of interest can be also modified using standard techniques that includes RNA-editing, chemical modifications, posttranslational and posttranscriptional modifications and the like. For instance, derivatives of the proteins of interest can be generated by processes such as altered phosphorylation, or glycosylation, or acetylation, or lipidation, or by different types of maturation cleavage and the like.

In certain embodiments, said mutant comprises at least one amino acid substitution that improved folding of the protein at 37° C., wherein said substitution is selected from the group consisting of R32G and S131P. In certain embodiments, said mutant comprises both substitutions.

In certain embodiments, said mutant further comprises one or more substitutions selected from the group consisting of E36G, K42R, F53V, K67R, T68A, L79F, I93V, F110L, N112D, I115L, R138L, G152S, H157R, Y169H, H1711, C172A, F174L, K188R, H193Y, M216V, K220R, and R231K, wherein said folding substitutions enhance protein folding and chromophore maturation rate at 37° C.

In certain embodiments, said mutant has modified N- and\or C-terminal part(s) and comprises at least one substitution from K6T and R231S, or both, wherein said substitutions reduce aggregation capacity of the mutant as compared with the corresponding wild type protein.

In some embodiments, said mutant is a longer variant of EqFP578, comprising additional N-terminal amino acid sequence selected from the group consisting of MGEY (SEQ ID NO:17) or MGED (SEQ ID NO:18), wherein said amino acid sequence reduces aggregation capacity of the mutant.

In certain embodiments, the functional fluorescent mutant of interest comprises at least one substitution selected from the group consisting of R155E, Q159D, S173N, F192V, and F194Y, wherein said mutant has reduced oligomerization capacity compared to wild type EqFP578. In a preferred embodiment, said functional fluorescent protein also comprises an N122R substitution that further reduces oligomerization capacity of the protein. In a preferred embodiment, said mutant comprises all noted substitutions and further comprises one or more substitutions selected from the group consisting of E36G, K42R, $F_{53}$V, K67R, T68A, L79F, 193V, F110L, N112D, I115L, R138L, G152S, H157R, Y169H, H1711, C172A, F174L, K188R, H193Y, M216V, K220R, and R231K, wherein those substitutions enhance protein folding and fluorescence intensity of the protein in vivo.

In some embodiments, the engineered functional fluorescent protein of the present invention comprises at least one substitution selected from the group consisting of H197R, S158G, N143S, N143H, N143F or N143Y, wherein said functional fluorescent protein has altered excitation and emission spectra compared to the corresponding wild type protein.

Specific mutants of interest include engineered functional fluorescent proteins comprising amino acid compositions of SEQ ID NOs: 4, 6, 8, 10, 12, 14, and 16 and are discussed in more detail in the experimental part, infra.

Also provided are proteins that are substantially the same as the above provided specific proteins, whereby substantially the same means that the protein has an amino acid sequence identity to the sequence of wild type protein of at least about 85% sequence identity, usually at least about 90% and more usually at least about 95%, (e.g. 95%; 96%, 97%; 98%: 99% or 100% sequence identity).

The proteins of the subject invention are present in a non-naturally occurring environment, e.g., are separated from their naturally-occurring environment or recombinant. The proteins of the present invention may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially purified form, where by "substantially purified form" means at least 95%, usually at least 97% and more usually at least 99% pure.

Fragments of the naturally-occurring protein as well as of the mutant and derivate proteins described above are also provided. Biologically active fragments and/or fragments corresponding to functional domains, and the like are of a particular interest. Fragments of interest are polypeptides that are typically at least about 30 amino acids in length, usually at least about 50 amino acids in length, preferably of at least about 75 or 100 amino acids in length and may be as long as 300 amino acids in length or longer, but will usually not exceed about 250 amino acids in length, where the fragment will have a stretch of amino acids that is identical to the subject protein of at least about 25 amino acids, and usually at least about 45 amino acids, and in many embodiments at least about 50 amino acids in length. In some embodiments, the subject polypeptides are about 25 amino acids, about 50, about 75, about 100, about 125, about 150, about 200, or about 250 amino acids in length, up to the entire length of the protein. In some embodiments, a protein fragment retains all or substantially all of the specific properties of the wild type protein or specific mutants thereof.

The subject proteins and polypeptides may be obtained from naturally occurring sources or synthetically produced. For example, wild type proteins may be derived from biological sources which express the proteins, e.g., *Entacmaea quadricolor*, such as the specific one listed above. The subject proteins may also be derived from synthetic means, e.g., by expressing a recombinant nucleic acid coding sequence encoding the protein of interest in a suitable host, as described above. Any convenient protein purification procedures may be employed, wherein suitable protein purification methodologies are described in Guide to Protein Purification, (Deuthser ed., Academic Press, 1990). For example, a lysate may be prepared from the original source and purified using HPLC, exclusion chromatography, gel electrophoresis, affinity chromatography, and the like.

Also provided are fusion proteins comprising a protein of the present invention, or fragments thereof, fused, for example, to a degradation sequence, a sequence of subcellular localization (e.g., nuclear localization signal, peroximal targeting signal, Golgi apparatus targeting sequence, mitochondrial targeting sequence, etc.), a signal peptide, or any protein or polypeptide of interest. Fusion proteins may comprise for example, a fluorescent protein of the subject invention polypeptide and a second polypeptide ("the fusion partner") fused in-frame at the N-terminus and/or C-terminus of the fluorescent protein. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the fluorescent protein portion of the fusion protein, and is typically not a *Entacmaea quadricolor* fluorescent protein of subject invention or derivative/fragment thereof; i.e., it is not found in *Entacmaea quadricolor* species.

Also provided are antibodies that bind specifically to the fluorescent proteins of the present invention. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, F(ab)$_2$ and Fab are also of interest.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g., *Escherichia coli, Streptomyces* sp., *Bacillus subtilis, Lactobacillus acidophilus*, etc) or eukaryotic host-cells. Transgenic organisms of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e., DNA) into such organisms are widely known and provided in references such as Sambrook et al. (Molecular Cloning: A Laboratory Manual, $3^{nd}$ Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example yeast. Yeast is widely used as a vehicle for heterologous gene expression (for example see Goodey et al Yeast biotechnology, D R Berry et al, eds, (1987) Allen and Unwin, London, pp 401-429) and by King et al Molecular and Cell Biology of Yeasts, E F Walton and G T Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2003) San Diego Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, wherein the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology (eds. Lea and Leegood, John Wiley & Sons) (1993) pp. 275-295 and in Plant Biotechnology and Transgenic Plants (eds. Oksman-Caldentey and Barz), (2002) 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The fluorescent proteins of the present invention (as well as other components of the subject invention described above) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In a preferred embodiment relating to the method for labeling a biological molecule, cell or cell organelle, the subject proteins find use as in vivo labels (or reporter molecules) in cell and molecular biology assays. The assays of interest include but not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as a biomolecule labels, or cell organelle labels in living and fixed cells; as a markers in cell or organelle fusion, as a cell or organelle integrity markers, as a transfection markers (e.g., as labels for selection of transfected cells containing an expression vector encoding at least one fluorescent protein of the invention), as real-time probes working at near physiological concentrations, etc.

Furthermore, the subject proteins may be used in a method for analyzing gene expression (e.g., promoter activity). In the other words, they find use for identifying and/or measuring the expression of a protein or polypeptide of interest in biological material. This method comprises: i) introducing into a cell a nucleic acid molecule comprising a nucleotide sequence encoding a fluorescent protein according to the present invention wherein said nucleic acid molecule is operatively linked to and under the control of an expression control sequence which moderates expression of said protein or polypeptide of interest; ii) expression of said nucleic acid under suitable conditions; and iii) detecting the fluorescence emission of the fluorescent protein as a means of measuring the expression of the protein of interest.

In particular, the subject proteins find use for identifying and/or measuring the expression and/or localization of protein or polypeptide of interest in biological material. This method comprises: i) introducing into a cell a nucleic acid molecule comprising a nucleotide sequence encoding a fluorescent protein according to the present invention wherein said nucleic acid molecule is fused with a sequence encoding a protein or polypeptide of interest and operatively linked to and under the control of an expression control sequence which moderates expression of said protein or polypeptide of interest; ii) culturing the cell under conditions suitable for the expression of the protein of interest; and iii) detecting the fluorescence emission of the fluorescent protein as a means of measuring the expression/localization of the protein of interest.

The applications of interest include the use of the subject proteins in fluorescence resonance energy transfer (FRET) methods. In these methods, the subject proteins serve as donor and/or acceptors in combination with a second fluorescent protein or dye with appropriate excitation/emission spectra; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; and 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins, and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to a phosphorylated/dephosphorylated domain of another protein), or the peptide has a $Ca^{2+}$ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; and 5,439,797; the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins also find use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with a shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130, 313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-activated fluorescence assays can be developed using the subject proteins, engineered to include a protease-specific cleavage sequence. Upon cleavage of the fluorescent protein by an activated protease, fluorescence would change due to conformational changes of the subject protein. The above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject fluorescent proteins also find use as biosensors, sources of circularly permuted fluorescent proteins and biosensors thereof. Methods of preparation and use of circularly permuted fluorescent proteins are described in Nagai et al., Proc Natl Acad Sci USA, 2001, V. 98(6), pp. 3197-3202, Nagai et al., Proc Natl Acad Sci USA, 2004, V. 101(29), pp 10554-10559, Filippin et al., J Biol. Chem., 2003, V. 278(40), pp. 39224-34, and U.S. Pat. Nos. 6,469,154 and 6,699,687, the disclosures of which are herein incorporated by reference. The biosensors can be used in prokaryotic and eukaryotic cells, such as a $Ca^{2+}$ ion indicators, a pH indicator, a phosphorylation indicator, other enzyme activity indicators, or as an indicator of ions, such as magnesium, sodium, potassium, chloride, halides, etc. Methods of using fluorescent proteins as biosensors also include those described in U.S. Pat. Nos. 5,972,638, 5,824,485, and 5,650,135 (as well as the references cited therein) the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. In preferred embodiments kits may be used for labeling a biological molecule. Kits typically include the protein of the invention as such, or a nucleic acid encoding the same preferably with the elements for expressing the subject proteins, for example, a construct such as a vector comprising a nucleic acid encoding the subject protein.

The following example is offered by way of illustration and not by way of limitation.

EXAMPLES

Example 1

Cloning of cDNA encoding a red fluorescent protein from *Entacmaea quadricolor*.

To search for fluorescent proteins from *Entacmaea quadricolor*, a strategy based on screening an expression cDNA library in *E. coli* was used. A small fragment (about 1 mm in length) of *Entacmaea quadricolor* (Eukaryota; Metazoa; Cnidaria; Anthozoa; Zoantharia; Actiniaria; Nynantheae; Actimidae; Entacmaea) tentacle that possessed bright red fluorescence was used for total RNA preparation. Total RNA was isolated by a NucleoSpin RNA II kit (Clontech). Amplified cDNA sample was prepared using a SMART cDNA amplification kit (Clontech) and cloned into the PCR-Script vector (Stratagene). About $5\times10^4$ recombinant clones were screened visually using a fluorescent stereomicroscope. As a result, a novel red fluorescent protein was identified named EqFP578 (or eqFP578, SEQ ID NOs: 1 and 2). The fluorescent protein shares approximately 76% amino acid sequence identity with another *Entacmaea quadricolor* fluorescent protein eqFP611 (GenBank Id AAN05449) and 64% amino acid sequence identity with nonfluorescent red protein asCP562 from *Anemonia sulcata* (GenBank Id AAG41206).

Example 2

Characterization of EqFP578 (SEQ ID NOS 1, 2)

The nucleic acid coding sequences of EqFP578 was obtained as described above in the Example 1 and cloned into a pQE30 expressing vector (Qiagen), so that the recombinant protein contained a six-histidine tag at its N-terminus. After expression in *E. coli*, the protein was purified via a metal-affinity resin TALON (Clontech) and characterized.

The protein has excitation-emission spectral peaks at 552 and 578 nm, respectively (FIG. 2). The purified protein possesses a molar extinction coefficient of 102,000 $M^{-1} cm^{-1}$ and a fluorescence quantum yield of 0.54. For the molar extinction coefficient determination, the mature chromophore concentration was estimated. Protein was alkali-denatured with an equal volume of 2M NaOH. Under these conditions, the DsRed-like chromophores (including EqFP578 chromophore) convert to the GFP-like chromophore, that absorbs at 446 nm with a molar extinction coefficient of 44,000 $M^{-1} cm^{-1}$ (Ward, W. W., Bioluminescence and Chemiluminescence (1981), Academic Press, 235-242). The absorption spectra for native and alkali-denatured EqFP578 were measured. The molar extinction coefficient for the native state protein was estimated based on the absorption of the denatured protein. For quantum yield determination, the fluorescence of EqFP578 was compared to equally absorbing DsRed2 with quantum yield 0.55.

The results of a gel-filtration test indicated that EqFP578 is a dimeric protein. Purified protein samples (~1 mg/ml) were loaded onto a Sephadex-100 column (0.7×60 cm) and eluted with a solution of 50 mM phosphate buffer (pH 7.0) and 100 mM NaCl. EGFP, HcRed1 and DsRed2 (Clontech) were used as monomer, dimer and tetramer standards, respectively. In addition, a tendency to form tetramers has been indicated when recombinant purified EqFP578 was used for the gel-filtration at concentration of about 10 mg/ml.

Example 3

Preparation of EqFP578 Mutants

In each case, the Diversity PCR Random Mutagenesis kit (CLONTECH) was used for random mutagenesis, under conditions optimal for 5-6 mutations per 1000 bp.

The wild type EqFP578 nucleic acid coding sequence was obtained as described above in the Example 1. To enhance expression in mammalian cells, we perform the following strategy: 1. random mutagenesis was used to find a protein with increased maturation speed and folding; 2. the protein sequence was "humanized"; 3. additional random mutagenesis was performed for further increasing maturation speed and brightness of the protein in E. coli at 37° C. As a result, EqFP578 mutant named EqFP578 ml was obtained (SEQ ID NOs: 3, 4) with mammalian-optimized codon usage and comprising six amino acid substitutions as compared with wild type EqFP578: R32G, T68A, L79F, L110F, S131P, and L138R.

Figure 3:
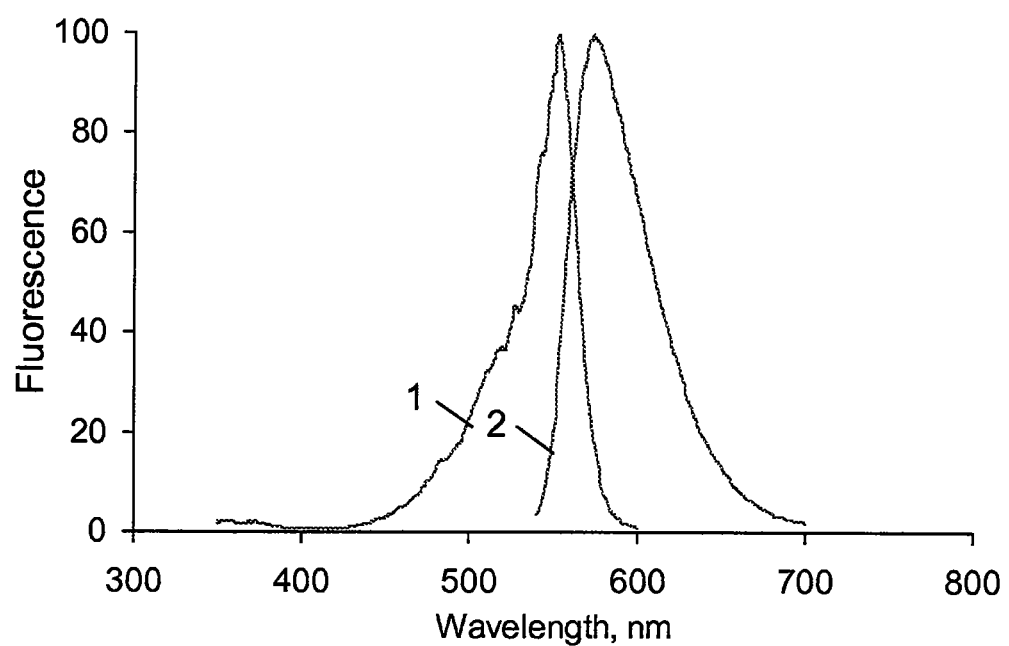
FIG. 3 illustrates the excitation (line 1) and emission (line 2) fluorescent spectra for EqFP578 ml mutant.

Recombinant EqFP578 ml was prepared, purified and characterized as described in the Example 2 for wild type EqFP578. Fluorescence properties of this mutant were similar, but not identical to the wild type EqFP578. It has excitation-emission spectral peaks at 553 and 574 nm, respectively (FIG. 3). Purified protein possesses a molar extinction coefficient of 104,000 $M^{-1} cm^{-1}$ and a fluorescence quantum yield of 0.65. Like wild type EqFP578, EqFP578 ml is a dimer.

While EqFP578 ml doesn't demonstrate any aggregation when expressed in vivo, it was shown to form aggregates in vitro, according to gel-electrophoresis data. This property can potentially restrict protein applications for generation stable cell lines and transgenic animals. To reduce aggregation capacity of the protein, the nucleic acid encoding them was subjected for additional modifications that increase local negative charge (i.e., concentration of negatively charged amino acid residues) at the protein C- and N-termini. In particular, amino acids at the N- and C-termini were substituted to reduce local positive charge, e.g., K6T and R231S substitutions were introduced by site directed mutagenesis. Further, an additional amino acid sequence (MGEY) was added to the protein N-terminus. Random mutagenesis of the nucleic acid obtained resulted in an additional K188R folding mutation that provides faster generation of a fluorescent signal in vivo, as shown upon expression of the protein in E. coli XL-1 Blue strain. Nucleotide and amino acid sequence of the non-aggregating mutant named M1-NA are shown in SEQ ID NOs: 5, 6, respectively.

Recombinant M1-NA was prepared, purified and characterized as described in the Example 2 for wild type EqFP578. According to gel-filtration data, M1-NA is a dimeric protein at a concentration of 1 mg/ml. Fluorescent properties of M1-NA are the same as those of EqFP578 ml. M1-NA is a bright red fluorescent protein, characterized with excitation/emission fluorescence spectra peaked at 553/574 nm. M1-NA fluorescence quantum yield=0.67, molar extinction coefficient (at 553 nm)=92,000 $M(-1)cm(-1)$. M1-NA doesn't form aggregates in vitro, according to gel-electrophoresis data. It also doesn't form any noticeable aggregates upon expression in eukaryotic cells, as it was shown for HeLa and 293T cell lines.

An EqFP578 ml variant (M1-602) with red-shifted excitation/emission spectra has been also produced by random mutagenesis. Comparing to EqFP578 ml, it comprises a N143S substitution, which provides a red shift of the fluorescence excitation and emission spectra. Random mutagenesis further yielded the substitutions F110L, I115L, R138L, G152S, and F174L that enhance protein folding and chromophore maturation, resulting in faster generation of a fluorescent signal in vivo as shown upon expression in E. coli XL-1 Blue strain. As well as M1-NA, M1-602 N- and C-termini were modified with substitutions K6T and R231S and addition of N-terminal amino acids (MGED). Nucleotide and amino acid sequence of the M1-602 protein are shown in SEQ ID NOs: 7, 8, respectively.

Figure 4:
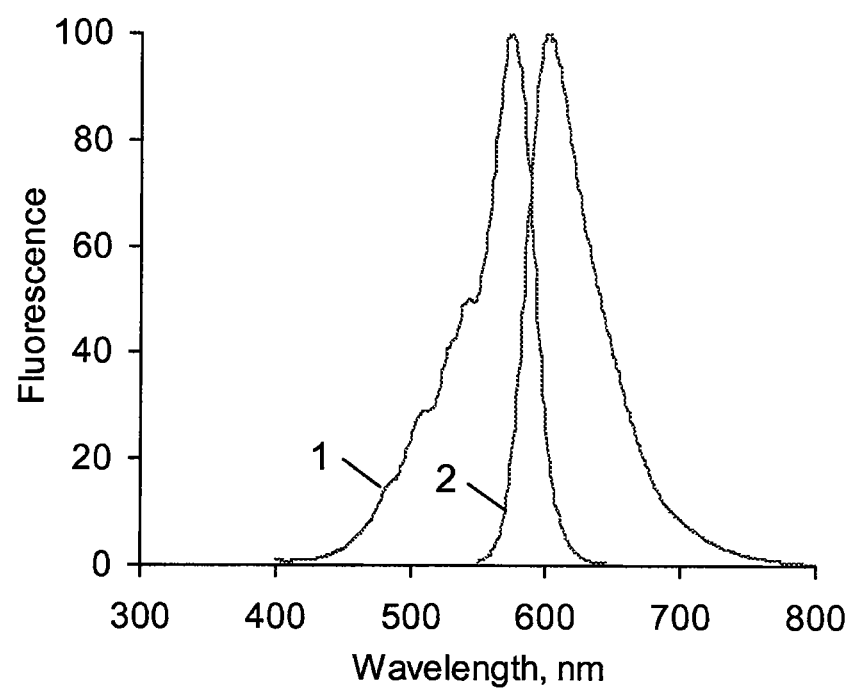
FIG. 4 illustrates the excitation (line 1) and emission (line 2) fluorescent spectra for M1-602 mutant.

Recombinant M1-602 was prepared, purified and characterized as described in the Example 2 for wild type EqFP578. It excitation/emission spectra peaked at 574/602 nm (see FIG. 4 for spectra). M1-602 nm fluorescence quantum yield=0.35, molar extinction coefficient (at 574 nm)=74,400 $M^{(-1)}cm^{(-1)}$. According to gel-filtration data, M1-602 nm is a dimeric protein at concentration of 1 mg/ml.

A mutant with an additional red-shift in the excitation/emission spectra named M1-637 has been prepared on the basis of the nucleic acid encoding M1-602 protein by site directed mutagenesis of the H197 and G158 residues. Comparing to M1-602, M1-637 comprises amino acid substitutions H197R and G158S, which provide a far-red shift of fluorescence spectra. Nucleotide and amino acid sequence of the M1-602 protein are shown in SEQ ID NOs: 9, 10, respectively.

Figure 5:
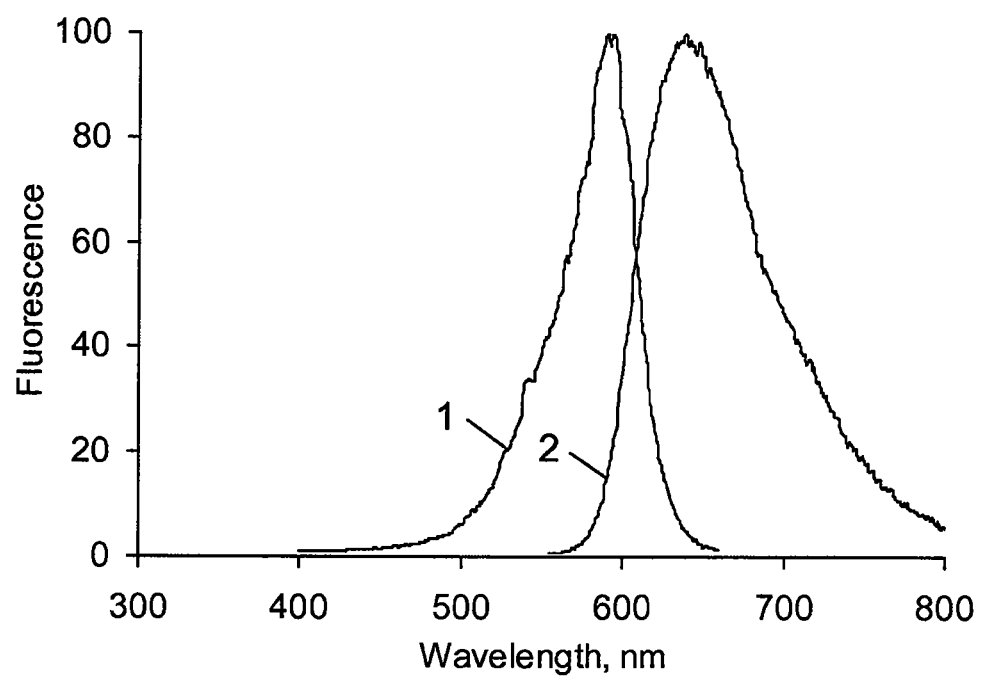
FIG. 5 illustrates the excitation (line 1) and emission (line 2) fluorescent spectra for M1-637 mutant.

Recombinant M1-637 was prepared, purified and characterized as described in the Example 2 for wild type EqFP578. M1-637 is a far-red fluorescent protein, characterized with excitation/emission fluorescence spectra peaked at 591/637 nm (see FIG. 5 for spectra). According to gel-filtration data, M1-637 is a dimeric protein at concentration of 1 mg/ml.

Due to its superior characteristics, EqFP578 and its mutants described above represent an attractive basis for the generation of a monomeric bright red fluorescent protein of advantageous properties. Availability of the crystal structure for the eqFP611 (Petersen et al., 2003, J Biol Chem v. 278: pp. 44626-44631), the close homologue of eqFP578, allowed us to determine amino-acid residues, responsible for the dimerization and weak tetramerization of eqFP578 and mutants thereof. Simultaneous site directed mutagenesis of several key amino acid residues, responsible for dimerization through the so called "second" or "hydrophilic" interface, i.e., R155E, Q159D, S173N, F192V and F194Y, has been employed on the nucleic acid encoding EqFP578 ml protein. Simultaneously, to adapt monomeric protein folding and maturation, random mutagenesis for the whole protein sequence was performed, while the key interface positions were fixed with primers. To inhibit the minor dimerization through the "first' ("hydrophobic") interface, the substitution N122R, which was reported to disrupt eqFP611 tetramerization efficiently, was also introduced (Wiedenmann et al., 2005, J Biomed Opt v. 10: p. 14003).

Figure 6:
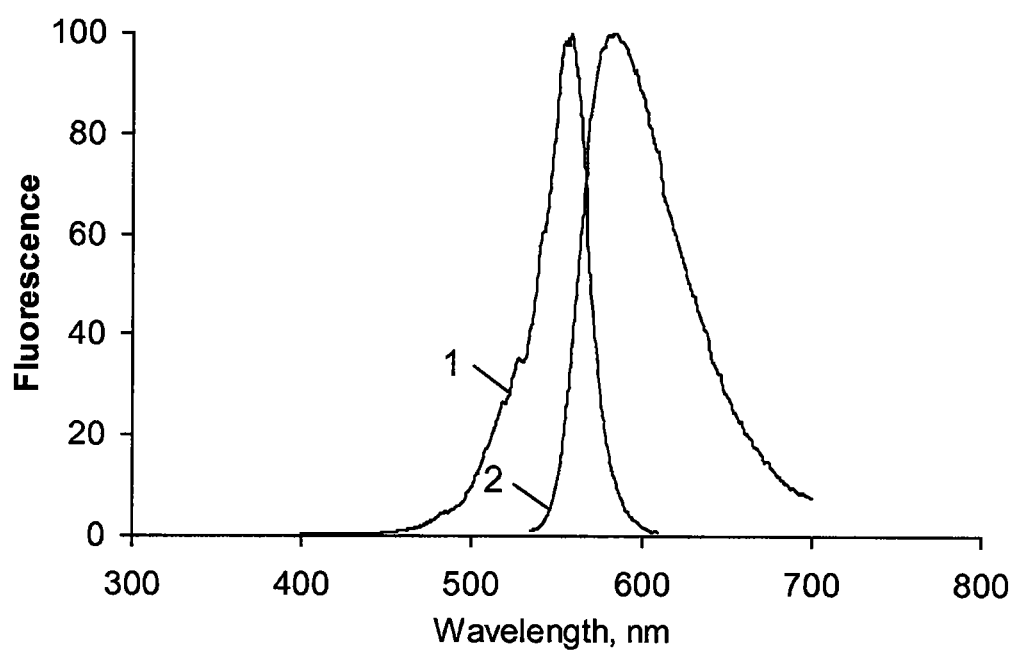
FIG. 6 illustrates the excitation (line 1) and emission (line 2) fluorescent spectra for M1-mono1 mutant.

Poorly maturating red fluorescent variants obtained after the first round of mutagenesis were checked by gel-filtration and shown to be monomeric, according to the gel-filtration data. This indicated that the introduced mutations were sufficient to disrupt dimerization. Then, an additional seven rounds of random mutagenesis were performed to optimize protein folding and maturation at 37° C. After every round the generated libraries were screened in an E. coli expression system, using a fluorescent stereomicroscope Olympus SZX-12, TRITC filter set. From 10 to 20 brightest clones were selected and checked by sequencing. Only those protein variants were used for the further work, which contained all key substitutions within the "second" interface. From 5 to 10 of the selected variants were compared in respect of fluorescence quantum yield, molar extinction coefficient and photostability. Completeness of the maturation of the red chromophore was checked by absorbance spectrum measurements. The final variant, M1-mono1, was a monomeric red fluorescent protein with excitation/emission peaked at 555/584 nm (FIG. 6). The nucleotide and amino acid sequence of the M1-mono1 protein are shown in SEQ ID NOs: 11, 12, respectively.

In addition, two cyan proteins were produced on the basis of M1-mono1. A nucleic acid encoding M1-mono1 was subjected to site-directed and a following random mutagenesis. The resulting plasmids encoding mutant fluorescent proteins were transfected into E. coli and the brightest cyan variants were selected. The first, nrM181-5, contains the substitutions N143H and R67K, which result in cyan fluorescence of the protein chromophore and protein capability of photoconversion to the red fluorescent form. As compared with M1-mono1, nrM181-5 also contains the substitutions R42K, C172A, V216M and R220K that enhance the protein folding and chromophore maturation. The nucleotide and amino acid sequence of the nrM181-5 protein are shown in SEQ ID NOs: 13, 14, respectively.

Figure 7:
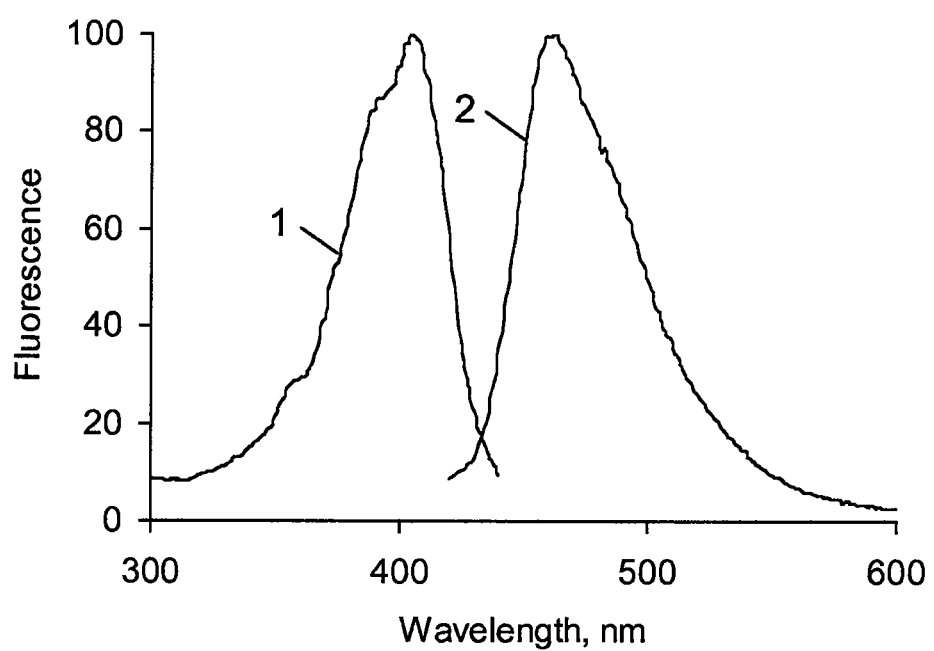
FIG. 7 illustrates the excitation (line 1) and emission (line 2) fluorescent spectra for nrM181-5 mutant (before photoconversion)

Recombinant nrM181-5 was prepared, purified and characterized as described in the Example 2 for wild type EqFP578. nrM181-5 is a cyan fluorescent protein, characterized with excitation/emission fluorescence spectra peaked at 400/470 nm (see FIG. 7 for spectra). According to gel-filtration data, nrM181-5 is a monomeric protein at a concentration of 1 mg/ml. The protein is capable of photoconversion to the red fluorescent form in response to violet light irradiation.

The second protein Cyan-2-1 comprises the substitutions N143F and H197Y, which result in cyan fluorescence of the protein chromophore. Cyan-2-1 also comprises substitutions E36G and F53V that enhance the protein folding and chromophore maturation. Nucleotide and amino acid sequence of the Cyan-2-1 protein are shown in SEQ ID NOs: 15, 16, respectively.

Recombinant Cyan-2-1 was prepared, purified and characterized as described in the Example 2 for wild type EqFP578. Cyan-2-1 is a cyan fluorescent protein, characterized with excitation/emission fluorescence spectra peaked at 400/470 nm. According to gel-filtration data, Cyan-2-1 is a monomeric protein at a concentration of 1 mg/ml. The protein is non-capable of photoconversion to the red fluorescent form in response to violet light irradiation.

Example 4

Polyclonal Antibody Preparation

Coding regions of nucleic acids of EqFP578 m1 prepared as described above in the Example 3 were cloned into pQE30 expressing vector (Qiagen), so that the recombinant protein contained a six-histidine tag at its N-terminus. After expression in E. coli, protein was purified by metal-affinity resin TALON (Clontech) under denaturing conditions. Rabbits were immunized and boosted four times at monthly intervals with recombinant polypeptides emulsified in complete Freund's adjuvant. Ten or 11 days after each boost the animals were bled. Polyclonal antiserum was tested on recombinant protein by ELISA and by Western immunoblotting.

Example 5

Mammalian Cell and Organelle Labeling Using EqFP578 Mutants

For fluorescent labelling of eukaryotic cells, the coding sequences of EqFP578 ml, M1-NA, M1-602, M1-637, M1-mono1, nrM181-5 and Cyan-2-1 prepared as described above in the Example 3 were cloned into pEGFP-N1 vector (CLONTECH) between AgeI and BglII restriction sites (in lieu of the EGFP-coding region). HeLa, 293T and Phoenix cell lines were transiently transfected with these vectors using LipofectAMINE reagent (Invitrogen) and tested 20 h after transfection. An Olympus CK40 fluorescence microscope equipped with a CCD camera (DP-50, Olympus) was used for cell imaging. Expression of each protein in all cell lines tested resulted in bright fluorescent signals without visible aggregation. Fluorescence was clearly detectable within 20 hours after transfection.

To test the proteins in fusions with subcellular localization signals, mitochondrial targeting sequence (MTS) from subunit VIII of human cytochrome c oxidase was cloned into the N1-vectors obtained as described above. Transfection of HeLa cells resulted in effective translocation of the proteins to the mitochondria of host cells. In each case, bright fluorescence was clearly detectable within 24 hours after transfection. No visible protein aggregation was observed.

Example 7

Protein Labeling Using EqFP578 Mutants

The coding sequences of EqFP578 ml, M1-NA, M1-602, M1-637, M1-mono1, nrM181-5 and Cyan-2-1 prepared as described above in the Example 3 were cloned into pEGFP-C1 vector (CLONTECH) in lieu of the EGFP-coding region. Coding sequences of fusion partners (human cytoplasmic beta-actin, fibrillarin and bid protein) were operatively linked with the sequences of EqFP578 mutants noted above by cloning of the fusion partner sequences into multiple cloning sites of the correspondent C-vectors in-frame with the coding sequences of fluorescent proteins. The vectors were transfected into HeLa cells. In each case, distribution of fluorescence reflected expected distribution of the fusion partner in a cell. Bright fluorescence was clearly detectable within 24 hours after transfection.

However, in the case of EqFP578 ml, M1-NA, M1-602, M1-637, abnormal distribution of the fluorescent signals was observed in host cells when alpha tubulin was used as a fusion partner. On the other hand, M1-mono1, nrM181-5 and Cyan-2-1 fusions with alpha tubulin showed an expected distribution of fluorescent signals suggesting monomeric nature of these proteins.

All publications and patent applications cited in this specification are incorporated by reference herein as if each individual publication or patent application were specifically and individually indicated to be incorporated by reference. The citation of any publication is to provide context and understanding of the present invention and should not be construed as an admission that any such publication is prior art.

What is claimed is:

1. An isolated nucleic acid encoding a functional fluorescent protein having an amino acid sequence that differs from the amino acid sequence of wild-type EqFP578 (SEQ ID NO:2) by at least one amino acid substitution selected from the group consisting of R155E, Q159D, S173N, and F192V.

2. The isolated nucleic acid according to claim 1, wherein the amino acid sequence of the encoded functional fluorescent protein differs from SEQ ID NO:02 by at least two or more amino acid substitutions selected from the group consisting of R155E, Q159D, S173N, and F192V.

3. The isolated nucleic acid according to claim 1, wherein the amino acid sequence of the encoded functional fluorescent protein differs from SEQ ID NO:02 by at least three or more amino acid substitutions selected from the group consisting of R155E, Q159D, S173N, and F192V.

4. The isolated nucleic acid according to claim 1, wherein the amino acid sequence of the encoded functional fluorescent protein differs from SEQ ID NO:02 by having the following amino acid substitutions: R155E, Q159D, S173N, and F192V.

5. The nucleic acid according to claim 1, wherein the amino acid sequence of the encoded functional fluorescent protein differs from SEQ ID NO:02 by further comprising a N122R substitution.

6. A vector comprising the nucleic acid according to claim 1.

7. An expression cassette comprising:
(a) a transcriptional initiation region functional in an expression host;
(b) the nucleic acid according to claim 1; and
(c) a transcriptional termination region functional in said expression host.

8. A host cell comprising the expression cassette according to claim 7 as part of an extrachromosomal element or integrated into the genome of a host cell as a result of introduction of the expression cassette into the host cell.

9. A transgenic cell comprising the nucleic acid according to claim 1.

* * * * *

UNITED STATES PATENT AND TRADEMARK OFFICE
CERTIFICATE OF CORRECTION

Page 1 of 2

PATENT NO.        : 8,563,703 B2
APPLICATION NO.   : 13/365137
DATED             : October 22, 2013
INVENTOR(S)       : Sergey A. Lukyanov et al.

It is certified that error appears in the above-identified patent and that said Letters Patent is hereby corrected as shown below:

In the Specification:

In Summary of the Invention:

Column 3, Line 15, please delete "S131 P" and insert -- S131P -- therefor;

Column 3, Line 22, please delete "193V" and insert -- I93V -- therefor;

Column 3, Line 24, please delete "H17II" and insert -- H171I -- therefor;

Column 3, Line 52, please delete "193V" and insert -- I93V -- therefor;

Column 3, Line 53, please delete "H17II" and insert -- H171I -- therefor;

Column 4, Line 32, please delete "193V" and insert -- I93V -- therefor;

Column 4, Line 33, please delete "H17II" and insert -- H171I -- therefor;

Column 4, Line 59, please delete "193V" and insert -- I93V -- therefor;

Column 4, Line 61, please delete "H17II" and insert -- H171I -- therefor;

Column 9, Line 50, please delete "Actimidae" and insert -- Actiniidae -- therefor;

Column 14, Line 27, please delete "Actimidae" and insert -- Actiniidae -- therefor;

Column 14, Line 67, please delete "193V" and insert -- I93V -- therefor;

Column 15, Line 1, please delete "H17II" and insert -- H171I -- therefor;

Column 15, Line 25, please delete "$F_{53}V$" and insert -- F53V -- therefor;

Column 15, Line 25, please delete "193V" and insert -- I93V -- therefor;

Signed and Sealed this
Eighteenth Day of February, 2014

Michelle K. Lee
*Deputy Director of the United States Patent and Trademark Office*

Column 15, Line 27, please delete "H1711" and insert -- H171I -- therefor;

Column 16, Line 63, please delete "F(ab)$_2$" and insert -- F(ab')$_2$ -- therefor;

In Examples:

Column 22, Line 43, please delete "Actimidae" and insert -- Actiniidae -- therefor;

Column 26, Line 31, please delete "AgeI" and insert -- Agel -- therefor;

Column 26, Line 31, please delete "BglII" and insert -- Bg/II -- therefor.